United States Patent [19]

Cerami et al.

[11] Patent Number: 4,822,776

[45] Date of Patent: Apr. 18, 1989

[54] LIPOPROTEIN LIPASE SUPPRESSION BY ENDOTOXIN-INDUCED MEDIATOR (SHOCK ASSAY)

[75] Inventors: Anthony Cerami, Flanders, N.J.; Masanobu Kawakami, Tokyo, Japan

[73] Assignee: The Rockefeller University, New York, N.Y.

[21] Appl. No.: 792,372

[22] Filed: Oct. 29, 1985

Related U.S. Application Data

[60] Division of Ser. No. 414,098, Sep. 7, 1982, which is a continuation-in-part of Ser. No. 351,290, Feb. 22, 1982, abandoned, which is a continuation-in-part of Ser. No. 299,932, Sep. 8, 1981, abandoned.

[51] Int. Cl.$^4$ .................. A61K 37/02; A61K 35/26; A61K 37/64
[52] U.S. Cl. .................................. 514/21; 530/350; 530/395; 530/417; 530/829; 530/838; 530/387; 514/8; 514/909; 424/85.8
[58] Field of Search .................. 530/350, 351; 424/85; 514/21

[56] References Cited

U.S. PATENT DOCUMENTS

4,309,418  1/1982  Green .................................. 530/380
4,684,623  8/1987  Larrick et al. ....................... 424/85

OTHER PUBLICATIONS

Charles A. Dinarello, Reviews of Infectious Diseases, at vol. 6, No. 1, (Jan.-Feb., 1984).
B. Beutler et al., Journal of Experimental Medicine, at vol. 161, pp. 984–995 (May, 1985, The Rockefeller University Press).
Fischer, C. L. et al., II: Serum Protein Abnormalities: Diagnostic and Clinical Aspects, eds. Ritzman, S. E. & Daniels, J. C. (Little Brown, Boston), pp. 331–350, (1975).
Brenneman, D. E. et al., Eur. J. Cancer 11, 225–230, (1975).
Barclay, M. et al., Prog. Biochem. Pharmacol. 10, 76–111, (1975).
Bagby, G. J. et al., Am. J. Physiol., 238, pp. 325–330, (1980).
Rouzer, C. A. et al., Mol. Biochem. Parasitol. 2, 31–38, (1980).
Kawakami, M. et al., J. Exp. Med. 154, 631–639, (1981).
Green, H. et al., Cell 1, 113–116, (1974).
Green, H. et al., Cell 5, 19–27, (1975).
Green, H. et al., Cell 7, 105–113, (1976).
Mackall, J. C. et al., J. Biol. Chem. 251, 6462–6464, (1976).
Student, A. K. et al., J. Biol. Chem. 255, 4745–4750, (1980).
Coleman, R. A. et al., J. Biol. Chem. 253, 7256–7261, (1978).
Wise, L. S. et al., Cell 13, 233–242, (1978).
Spooner, P. M. et al., J. Biol. Chem. 254, 1305–1311 (1979).

(List continued on next page.)

Primary Examiner—Delbert R. Phillips
Assistant Examiner—Jeff. P. Kushan
Attorney, Agent, or Firm—Klauber & Jackson

[57] ABSTRACT

A mediator substance exhibiting inhibitory effect upon anabolic enzyme activity in mammals, is prepared by a method comprising gathering a sample of macrophage cells from a mammal, incubating a portion of the macrophage cells with a stimulating material that is associated with an invasive event, and inducing the macrophage cells to produce the mediator substance. The stimulator materials, for example, may include endotoxins, trypanosomes and the like, and the enzymes that may be observed range from lipoprotein lipase, acetyl Coenzyme A carboxylase and fatty acid synthetase, to the inducers for red blood cells growth and differentiation. The mediator substance may be utilized to raise antibodies which would in turn find utility in testing for the presence or amount of various invasive stimuli, such as infection and the like. Testing procedures and appropriate materials in kit form are also contemplated. The mediator substance may likewise be utilized in procedures as a screening agent, to test for potentially effective anti-shock agents or chemicals.

2 Claims, 10 Drawing Sheets

OTHER PUBLICATIONS

Eckel, R. H. et al., Biochem. Biophys. Res. Commun. 78, 288-293, (1977).
Eckel, R. H. et al., Biochem. Biophys. Res. Commun. 84, 1069-1075, (1978).
Spooner, P. M. et al., J. Biol. Chem. 254, 10021-10029, (1979).
Westphal, O. et al., in Method in Carbohydrate Chemistry, eds. Whistler, R. L. BeMiller, J. N. & Wolfrom, M. L., Academic, New York) vol. 5, pp. 83-91, (1965).
Rubin, C. S. et al., J. Biol. Chem. 253, 7570-7578 (1978).
Edelson, P. J. et al., J. Exp. Med. 142, 1150-1164 (1975).
Olivecroma, T. et al., Fed. Proc. Fed. Am. Soc. Exp. Biol. 36, 60-65.
Nilsson-Ehle, P. et al., J. Lipid Res. 17, 536-541, (1976).
Korn, E. D., J. Biol. Chem. 215, 1-14 (1955).
Korn, E. D., J. Biol. Chem. 215, 15-26 (1955).
Chaudry, I. H. et al., Arch. Surg. 109, 412-415 (1978).
Sipe, J. D. et al., J. Exp. Med. 150, 597-606 (1979).
Werner, M., Clin. Chem. Acta. 25:299 (1969).
McAdam, K. P. W. J. et al., Lancet II:572 (1975).
Rosenthal, C. J. et al., J. Clin. Invest. 55:746 (1975).
Fielding, C. J. et al., Arch. Pathol. Lab. Med. 101:225 (1977).
Gallin, J. I. et al., N. Engl. J. Med. 281:1081 (1969).
Farshtchi, D. et al., J. Bacteriol. 95:1615 (1968).
Grossberg, S. E. et al., Nature (London) 208:954 (1965).
Sultzer, B. M. Nature (London) 219:1253 (1968).
Kampschmidt, R. F. et al., J. Lab. Clin. Med. 95:616-623 (1980).
Pykälistö, O. J. et al., (1975) Proc. Soc., Exp. Biol. Med. 148: (1975).
Taskinen, M. et al., Diabetologia 17:351 (1979).
Herring, W. B. et al., J. Clin. Invest. 42:79 (1963).
Carey, F. J. et al., J. Clin. Invest. 37:441 (1958).
Havel, R. J. et al., J. Clin. Invest. 39:1777 (1960).
Pykälistö, O. J. et al., J. Clin. Invest. 56:1108 (1975).
Cameron, D. J. et al., J. Clin. Invest. (JCINA), 63 (5), pp. 972-984 (1979).
Johnson, H. M. et al., Cell Immunol. (CLIMB), 44 (1) pp. 125-130 (1979).
Sethi, K. K. et al., Arch. Virol. (ARVID), 59 (3) pp. 157-172 (1979).
Zubler, R. H. et al., Fed. Proc. (FEPRA), 38 (3 Part 1), 1276.
Kaliner, M., Am. Rev. Respir. Dis (ARDSB), 118 (6 Part 1), Received 1979) pp. 1015-1022 (1978).
Cohen, S., Am. J. Pathol. (AJPAA), 88 (3) pp. 502-528 (1977).
Kempf, K. E. et al., J. Immunol. (JOIMA), 119 (2) pp. 517-523 (1977).
Gallin, E. K. et al., Cell Immunol. (CLIMB) 27 (2) at 348 (1976).
Plescia, O. J. Cell Immunol. (CLIMB) 27 (2) at 348-349 (Received 1977) (1976).
Okpako, D. T., Int. Arch. Allergy Appl. Immunol. (IAAAA) 40 (4-5) pp. 620-630 (1971).
Krejci, J. et al., Folia. Microbiol. (FOMIA) 13 (6) p. 562.
Itkin, I. H. et al., J. Allergy (JOALA), 41 (2) pp. 88-89 (1968).
Keenan, R. A. et al., 65th Annual Meeting of the Federation of American Societies for Experimental Biology, Atlanta, Ga., U.S.A., Apr. 12-17, 1981, Fed. Proc. (FEPRA), 40 (3 Part 1), p. 439 (1981).
Kampschmidt, R. F. et al., J. Reticuloendothel. Soc. (RESJA) 28 (2) pp. 191-201 (1980).
Atkins, P. C. et al., J. Allergy Clin. Immunol. (JACIB), 64 (4) pp. 251-258 (1979).
Skarnes, R. C. et al., J. Exp. Med. (JEMEA) 154 (4) pp. 1212-1228 (1981).
Bornstein, D. L. et al., 38th. Annual National Meeting of the American Federation for Clinical Research, San Francisco, Calif., U.S.A., Apr. 25-1981, Clin. Res. (CLREA), 29 (2) p. 381A (1981).
Yang, R. D. et al., 65th. Annular Meeting of the Federation of American Society for Experimental Biology, Atlanta, Ga., U.S.A., Apr. 12-17, 1981, Fed. Proc. (FEPRA), 40 (3 Part 2), p. 901 (1981).
Juniper, E. F. et al., Clin. Allergy (CLAGB), 11 (1) pp. 61-66 (1981).
Barney, C. C. et al., Lipton, J. M. (Ed.). Fever: International Symposium, Dallas, Tex., U.S.A., Apr. 11-12, 1979, XII+263P, Raven Press: New York, Illus. ISBN 0-89004-451-1 (08877), 0 (0), pp. 111-122 (1980).
Kampschmidt, R. F., Lipton, J. M. (Ed.), Fever: International Symposium, Dallas, Tex., U.S.A., Apr. 11-12, 1979, XII+263P, Raven Press: New York, U.S.A., Illus. ISBN 0-89004-451-1 (08877) 0 (0), pp. 49-56 (1980).
Selvan, R. et al., Indian J. Biochem. Biophys. (IJBBB), 15 (2) pp. 115-121 (1978).

(List continued on next page.)

OTHER PUBLICATIONS

Eckel, R. H. et al., Biochem. Biophys. Res. Commun. 78, 288–293, (1977).
Eckel, R. H. et al., Biochem. Biophys. Res. Commun. 84, 1069–1075, (1978).
Spooner, P. M. et al., J. Biol. Chem. 254, 10021–10029, (1979).
Westphal, O. et al., in Method in Carbohydrate Chemistry, eds. Whistler, R. L. BeMiller, J. N. & Wolfrom, M. L., Academic, New York) vol. 5, pp. 83–91, (1965).
Rubin, C. S. et al., J. Biol. Chem. 253, 7570–7578 (1978).
Edelson, P. J. et al., J. Exp. Med. 142, 1150–1164 (1975).
Olivecroma, T. et al., Fed. Proc. Fed. Am. Soc. Exp. Biol. 36, 60–65.
Nilsson-Ehle, P. et al., J. Lipid Res. 17, 536–541, (1976).
Korn, E. D., J. Biol. Chem. 215, 1–14 (1955).
Korn, E. D., J. Biol. Chem. 215, 15–26 (1955).
Chaudry, I. H. et al., Arch. Surg. 109, 412–415 (1978).
Sipe, J. D. et al., J. Exp. Med. 150, 597–606 (1979).
Werner, M., Clin. Chem. Acta. 25:299 (1969).
McAdam, K. P. W. J. et al., Lancet II:572 (1975).
Rosenthal, C. J. et al., J. Clin. Invest. 55:746 (1975).
Fielding, C. J. et al., Arch. Pathol. Lab. Med. 101:225 (1977).
Gallin, J. I. et al., N. Engl. J. Med. 281:1081 (1969).
Farshtchi, D. et al., J. Bacteriol. 95:1615 (1968).
Grossberg, S. E. et al., Nature (London) 208:954 (1965).
Sultzer, B. M. Nature (London) 219:1253 (1968).
Kampschmidt, R. F. et al., J. Lab. Clin. Med. 95:616–623 (1980).
Pykälistö, O. J. et al., (1975) Proc. Soc., Exp. Biol. Med. 148: (1975).
Taskinen, M. et al., Diabetologia 17:351 (1979).
Herring, W. B. et al., J. Clin. Invest. 42:79 (1963).
Carey, F. J. et al., J. Clin. Invest. 37:441 (1958).
Havel, R. J. et al., J. Clin. Invest. 39:1777 (1960).
Pykälistö, O. J. et al., J. Clin. Invest. 56:1108 (1975).
Cameron, D. J. et al., J. Clin. Invest. (JCINA), 63 (5), pp. 972–984 (1979).
Johnson, H. M. et al., Cell Immunol. (CLIMB), 44 (1) pp. 125–130 (1979).
Sethi, K. K. et al., Arch. Virol. (ARVID), 59 (3) pp. 157–172 (1979).
Zubler, R. H. et al., Fed. Proc. (FEPRA), 38 (3 Part 1), 1276.
Kaliner, M., Am. Rev. Respir. Dis (ARDSB), 118 (6 Part 1), Received 1979) pp. 1015–1022 (1978).
Cohen, S., Am. J. Pathol. (AJPAA), 88 (3) pp. 502–528 (1977).
Kempf, K. E. et al., J. Immunol. (JOIMA), 119 (2) pp. 517–523 (1977).
Gallin, E. K. et al., Cell Immunol. (CLIMB) 27 (2) at 348 (1976).
Plescia, O. J. Cell Immunol. (CLIMB) 27 (2) at 348–349 (Received 1977) (1976).
Okpako, D. T., Int. Arch. Allergy Appl. Immunol. (IAAAA) 40 (4–5) pp. 620–630 (1971).
Krejci, J. et al., Folia. Microbiol. (FOMIA) 13 (6) p. 562.
Itkin, I. H. et al., J. Allergy (JOALA), 41 (2) pp. 88–89 (1968).
Keenan, R. A. et al., 65th Annual Meeting of the Federation of American Societies for Experimental Biology, Atlanta, Ga., U.S.A., Apr. 12–17, 1981, Fed. Proc. (FEPRA), 40 (3 Part 1), p. 439 (1981).
Kampschmidt, R. F. et al., J. Reticuloendothel. Soc. (RESJA) 28 (2) pp. 191–201 (1980).
Atkins, P. C. et al., J. Allergy Clin. Immunol. (JACIB), 64 (4) pp. 251–258 (1979).
Skarnes, R. C. et al., J. Exp. Med. (JEMEA) 154 (4) pp. 1212–1228 (1981).
Bornstein, D. L. et al., 38th. Annual National Meeting of the American Federation for Clinical Research, San Francisco, Calif., U.S.A., Apr. 25–1981, Clin. Res. (CLREA), 29 (2) p. 381A (1981).
Yang, R. D. et al., 65th. Annular Meeting of the Federation of American Society for Experimental Biology, Atlanta, Ga., U.S.A., Apr. 12–17, 1981, Fed. Proc. (FEPRA), 40 (3 Part 2), p. 901 (1981).
Juniper, E. F. et al., Clin. Allergy (CLAGB), 11 (1) pp. 61–66 (1981).
Barney, C. C. et al., Lipton, J. M. (Ed.). Fever: International Symposium, Dallas, Tex., U.S.A., Apr. 11–12, 1979, XII+263P, Raven Press: New York, Illus. ISBN 0-89004-451-1 (08877), 0 (0), pp. 111–122 (1980).
Kampschmidt, R. F., Lipton, J. M. (Ed.), Fever: International Symposium, Dallas, Tex., U.S.A., Apr. 11–12, 1979, XII+263P, Raven Press: New York, U.S.A., Illus. ISBN 0-89004-451-1 (08877) 0 (0), pp. 49–56 (1980).
Selvan, R. et al., Indian J. Biochem. Biophys. (IJBBB), 15 (2) pp. 115–121 (1978).

(List continued on next page.)

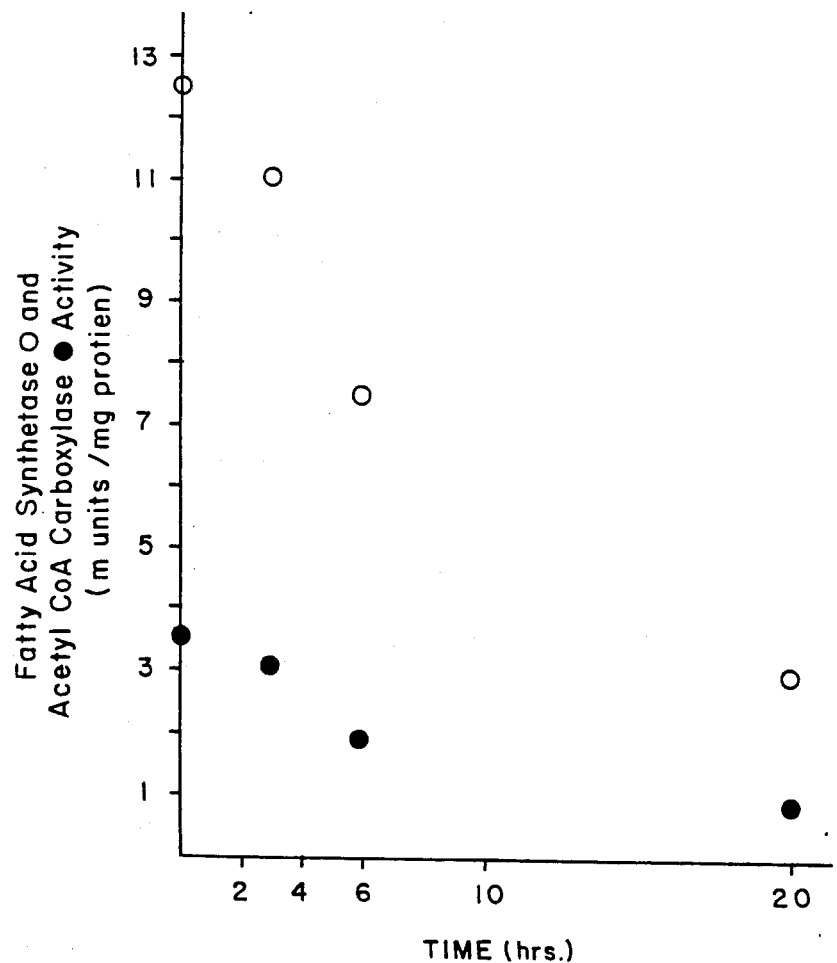
FIG.4: Effect of conditioned medium from endoxin-treated mouse peritoneal exudate cells on the activities of acetyl CoA carboxylase and fatty acid synthetase in 3T3-L1 cells.

FIG. 5A & 5B: Effect of mediator that suppresses the synthesis of fatty acid synthetase.

FIG-6A
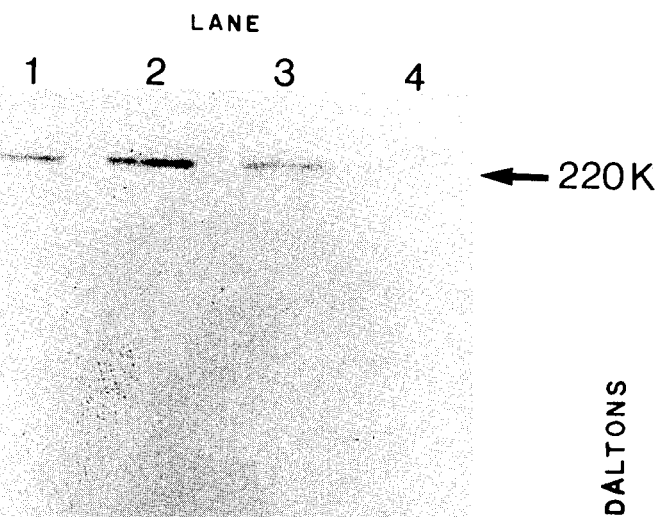
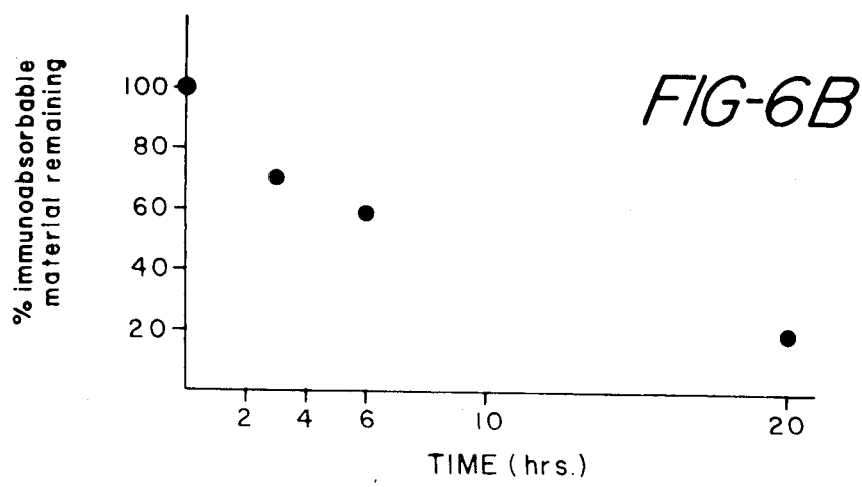
FIG-6B
FIG. 6A & 6B: Effect of mediator that suppresses the synthesis of acetyl CoA carboxylase.

FIG.8 Effect of mediator on protein synthesis in the cystosolic fraction of the cells.

FIG. 9: Effect of mediator on protein synthesis in the membrane fraction of the cells.

LIPOPROTEIN LIPASE SUPPRESSION BY ENDOTOXIN-INDUCED MEDIATOR (SHOCK ASSAY)

This invention was made in the course of a grant from the National Institutes of Health.

RELATED APPLICATIONS

The instant application is a division of Ser. No. 414,098, filed Sept. 7, 1982, which is in turn continuation-in-part of Ser. No. 351,290, now abandoned, filed Feb. 22, 1982, by the same applicants, which in turn is a continuation-in-part of Ser. No. 299,932, now abandoned, filed Sept. 8, 1981. Applicants claim the benefit of these applications under 35 U.S.C. §120.

RELATED PUBLICATIONS

The applicants are authors or coauthors of two articles directed to the subject matter of the instant invention: (1) [applicants only] "Studies of Endotoxin-Induced Decrease in Lipoprotein Lipase Activity", J. EXP. MED. 154 at 631-639 (September, 1981, published after Sept. 8, 1981), incorporated herein by reference; and (2) [co-authors with Phillip H. Pekala and M. Daniel Lane]: "Lipoprotein Lipase Suppression in 3T3-L1 Cells by an Endotoxin-Induced Mediator from Exudate Cells", PROC. NAT'L. ACAD. SCI. 79 at 912-916 (February, 1982, published after Feb. 22, 1982), also incorporated herein by reference.

BACKGROUND OF THE INVENTION

1. Field of the Invention

The present invention is directed generally to methods and associated materials for analysis of the effect and operation of invasive stimuli upon animal hosts, and in particular, is concerned with the mechanism and magnitude of the effect that such invasive stimuli may exert upon the activity of anabolic enzymes present in the host.

2. Description of the Prior Art

Several common physiological and biochemical derangements have been seen in various mammalian hosts responding to variety of invasive stimuli such as bacterial, viral and protozoan infections, as well as tumors and endotoxemia. For example, these responses include fever, leukocytosis, hyperlipidemia, reduced food intake and activity, and other modifications in muscle, white blood cell and liver metabolism. Recently, a hypertriglyceridemia in rabbits infected with a protozoan parasite, *Trypanosoma brucei* was reported by C. A. Rouser and A. Cerami, MOL. BIOCHEM. PARASITOL. 1 at 31-38 (1980). The reported hypertriglyceridemia was accompanied by a marked decrease in the activity of the enzyme lipoprotein lipase (LPL) in peripheral tissues.

LPL activity has been observed by others, and it has been noted that this condition has existed when the human body was in shock. See E. B. Man, et al, "The Lipids of Serum and Liver in Patients with Hepatic Diseases", J. CLIN. INVEST. 24 at 623, et seq. (1945); See also John I. Gallin, et al, "Serum Lipids in Infection", N. ENGL. J. MED. 281 at 1081-1086 (Nov. 13, 1969); D. Farstchi, et al., "Effects of Three Bacterial Infections on Serum Lipids of Rabbits", J. BACTERIOL. 95 at 1615, et seq. (1968); S. E. Grossberg, et al., "Hyperlipaemia Following Viral Infection in the Chicken Embryo: A New Syndrome", NATURE (London) 208 at 954, et seq. (1965); Robert L. Hersch, et al., "Hyperlipidemia, Fatty Liver and Bromsulfophthalein Retention in Rabbits Injected Intravaneously with Bacterial Endotoxin", J. LIPID. RES. 5 at 563-568 (1964); and Osamu Sakaguchi, et al., "Alterations of Lipid Metabolism in Mice Injected with Endotoxins", MICROBIOL. IMMUNOL. 23 (2) at 71-85 (1979); R. F. Kampschmidt, "The Activity of Partially Purified Leukocytic Endogeneous Mediator in Endotoxin-Resistant C3H/HeJ Mice", J. LAB. CLIN. MED. 95 at 616, et seq. (1980); and Ralph F. Kampschmidt, "Leukocytic Endogeneous Mediator", J. RET. SOC. 23 (4) at 287-297 (1978).

While the existence of "mediators" was at least suspected, the effect, if any, that they had on general anabolic activity of energy storage cells was not known. The present applicants suspected that these "mediators" exerted a depressive effect upon the activity of certain anabolic enzymes, whose reduced activity was observed in instances where the host entered the condition of shock in response to invasion. Thus, the relationship of the mediator produced by endotoxin-stimulated peritoneal mouse exudate cells, upon endotoxin-sensitive and endotoxin-insensitive mice alike, and the development through this investigation, of a reagent for measuring anabolic enzyme activity, was set forth in Ser. No. 299,932, and the further investigation of this system in conjunction with the 3T3 L1 "preadipocyte" model system, and the corresponding development of methods and associated materials for developing antibodies to the "mediators" as well as screening procedures for the identification and development of drugs capable of controlling the activity of these "mediators" was set forth in application Ser. No. 351,290. The work done to date indicates that a need exists for methodology and associated diagnostic materials, to enable further investigation of the "mediator" phenomenon to proceed, as well as to provide practical diagnostic tools useful in the treatment of the adverse sequelae of infection and concomitant shock.

SUMMARY OF THE INVENTION

In accordance with a first aspect of the present invention, a method for preparing a mediator substance for use in assessing the state of anabolic enzymes in mammals, is disclosed, which finds particular utility in the instance where the mammals are undergoing invasive stimmuli such as, viral agents, bacteria, protozoa, tumors, endotoxemia and others. In its simplest aspect, the method comprises gathering a sample of macrophage cells from a mammal and incubating a portion of the macrophage cells with a stimulator material associated with an invasive event. For example, the stimulator material may be endotoxin, in the instance of endotoxemia, trypanosomes, in the instance of the above mentioned protozoan parasite *Trypanosoma brucei*, and others.

While the peritoneal exudate cells illustrated in our present and previous applications exemplify sources for the macrophage cells, it is to be understood that such cells may be gathered from other than the peritoneal area, and that the present invention contemplates such variation within its scope.

The macrophage cells and the stimulator material are incubated as indicated, and thereafter, the macrophage cells are induced to produce a mediator substance capable of supressing the activity of the anabolic enzymes. Preferably, the inducement of mediator production is accomplished during the incubation period which may, for example, extend up to about 20 hours. The resulting medium may be appropriately treated to recover the mediator substance, and, for example, may be centrifuged, and the supernatant containing the mediator substance drawn off, or the mediator may be precipitated with a 40-60% solution of ammonium sulfate.

As mentioned earlier, the mediator substance has a broad range of effects, including inhibitive effects that have been observed with respect to anabolic enzymes such as lipoprotein lipase (LPL), acetyl Coenzyme A carboxylase, fatty acid synthetase, and the like. Also inhibitive effects have been found with red blood cell formation, as the mediator substance has been found to be capable of inhibiting the growth and differentiation of erythroid committed cells, by the suppression of a number of growth and differentiation inducers, such as dimethylsulfoxide (DMSO), hexamethylene bisacetamide, butyric acid, hypoxanthine and the like, as illustrated later on herein in specific examples.

A further embodiment of the present invention comprises a method for detecting various invasive stimuli by their capability of inhibiting the activity of one or more anabolic enzymes. In this method, a plurality of macrophage cell samples, may be prepared and selectively innoculated with a number of known stimulator materials, each characteristic in its effect upon differing anabolic actors. One of the macrophage samples may be innoculated with material from the presumed situs of the infective stimulus, and all samples may thereafter be incubated in accordance with the method described above. Thereafter, testing of each of the supernatants with the mediator substances derived from the known stimulator materials, would provide a comparative continuum for the identification of any invasive stimulus found present. This testing method may utilize the 3T3 L1 cell system, for example, in the instance where lipoprotein lipase (LPL) activity is utilized as a parameter. Likewise, in the instance where red cell inducers are utilized, the Friend virus-transformed erythroleukemia cells may be innoculated and thereafter observed. See Friend, C., Sher, W. Holland J. G. and Sato, G. PROC. NATL. ACAD. SCI. 68, at 378-382; Marks, P. A., Rifkind, R. A., Terada, M., Ruben, R. C., Gazitt, Y. and Fibach, E. in ICN-UCLA Symposia on Molecular and Cellular Biology, Vol. X. "Hematopoietic Cell Differentiation". Ed. by D. W. Golde, M. J. Kline, D. Metcalf and C. F. Fox (Academic Press, New York), pp. 25-35 (1978). Naturally, other cellular systems may be utilized in the instance where specific activities may be appropriately observed, and the invention is not limited to the specific cellular systems set forth herein.

The invention includes methods for detecting the presence of samples of the various invasive stimuli in mammals by measuring mediator substance activity in the mammals. Thus, a number of mediator substance may be prepared from the incubation of individual cell samples with known stimulator materials, and these mediator samples may thereafter be used to raise antibodies capable of specifically detecting the presence of the respective mediator substances. These antibodies may be prepared by known techniques, including the well known hybridoma technique for example, with fused mouse spleen lymphocytes and myeloma, or by development in various animals such as rabbits, goats and other mammals. The known mediator samples and their antibodies may be appropriately labelled and utilized to test for the presence of the mediator substance in, for example, serum, as one may measure the degree of infection, and determine whether infection is increasing or abating, by observing the activity of the mediator substance therein. A variety of well known immunological techniques may be utilized in accordance with this aspect of the present invention, including single and double antibody techniques, utilizing detectible labels associated with either the known mediator substances, or their respective associated antibodies.

A further embodiment of the present invention relates to a method for preventing the occurence of shock in mammals, comprising detecting the presence and shock promoting activity of a mediator substance in the mammal, and thereafter administering an antibody to the mediator substance, in an amount effective to prevent the development of shock in the mammal.

Also, an assay system is disclosed and may be prepared for the screening of drugs potentially effective to inhibit the synthesis or activity of the mediator substance. In the former instance, the effect of the test drug on the production of mediator by stimulated macrophages is determined. In the latter instance, a mediator substance may be introduced to cellular test systems, such as the 3T3 L1 cells, and the prospective drug may then be introduced to the resulting cell culture and the culture thereafter examined to observe any changes in mediator activity, either from the addition of the prospective drug alone, or the effect of added quantities of the known mediator substance.

A number of materials, compounds and agents have already been tested to determine their effect if any on mediator substance production and activity. As discussed in further detail in the description, infra., only the steroid dexamethasone exhibited any inhibitory effect, and that effect appeared to be limited to the production of the mediator substance. Further agents, drugs, etc., can however be tested in the manner such as that employed with dexamethasone, and described herein.

The preparation of the mediator substance, and the determination of the importance of its activity, has resulted in the development of numerous avenues of diagnostic and therapeutic application. It is clear from the foregoing and following, that the detection of invasive stimuli may be made by the identification of the mediator substance, either directly or through the development of antibodies useful in immunological diagnosis. Further, these same antibodies may be utilized for direct treatment by control of mediator activity, to avert the development of shock in mammals, while the mediator substance may be utilized as screening agents in an assay system for the identification of drugs, agents and other substance capable of neutralizing the adverse effects of the mediator substance, and thereby providing treatment of the adverse sequelae of infection.

Accordingly, it is a principal object of the present invention to provide a method for the preparation of a mediator substance exhibiting suppressive effects upon anabolic enzyme activity in mammals.

It is a further object of the present invention to provide a method for detecting the presence of a mediator substance in mammals in which invasive stimuli such as infection are suspected to be present.

It is a further object of the present invention to provide a method and associated assay system, for screening substances, such as drugs, agents and the like, potentially effective in combating the adverse effects of the mediator substance in mammals.

It is yet further object of the present invention to provide a method for the treatment of mammals to control the activity of said mediator substance so as to mitigate or avert the adverse consequences of their activity.

Other objects and advantages will become apparent to those skilled in the art from a review of the ensuing description, which proceeds with reference to the following illustrative drawings.

DESCRIPTION OF THE DRAWINGS

FIG. 4 shows the effect of conditioned medium from endotoxin-treated mouse peritoneal exudate cells on the activities of acetyl CoA carboxylase and fatty acid synthetase in 3T3-L1 cells. Three hundred (300) $\mu$l of conditioned medium was added to cultures of 3T3-L1 cells ($4.2 \times 10^6$ cells/dish) in 6 cm dishes containing 3.5 ml of DME medium and 10% fetal calf serum. After the indicated times of incubation, the enzymatic activity of acetyl CoA carboxylase (identified by the symbol "●") and fatty acid synthetase (identified by the symbol "o") on a digitonin releaseable cytosolic fraction of the cells was assessed.

FIG. 6 shows the effect of a mediator that suppresses the synthesis of fatty acid synthetase. Experimental design is identical to that described in the legend to FIG. 5. Panel A: Autoradiogram of a 7.5%-acrylamide-SDS gel analysis of immunoadsorbable fatty acid synthetase. Lane 1—control, without exposure to mediator; Lanes 2, 3, and 4, exposure of the cells to the mediator for 3, 6 and 20 hours, respectively. Panel B: Results of a densitometric scan of the autoradiogram, indicating percent of immunoadsorbable material remaining relative to control after exposure to the mediator.

Friend cells (clone DS-19) were incubated for 96 hours in the absence or in the presence of Me$_2$SO (1.5 vol %). Conditioned media (80 $\mu$l/ml of growth medium) from mouse peritoneal macrophage cultures stimulated or not stimulated with endotoxin (5 $\mu$g/ml) were added at the beginning of culture. Cell members were counted with a Cytograf model 6300 and expressed as percent inhibition of the control cells. Cell number in untreated control culture was $3 \times 10^6$ cells/ml. Heme content was determined fluorometrically as described previously (Sassa, S., Granick, S., Chang, C. and Kappas, A. (1975) In Erythropoiesis, ed. by K. Nakao, J. W. Fisher and F. Takaku (University of Tokyo Press, Tokyo) pp. 383–396). Data are the mean of duplicate determinations. The number of trypan blue positive cells assessed by Cytograf counting was 8-10% for all cultures.

Figure 11:
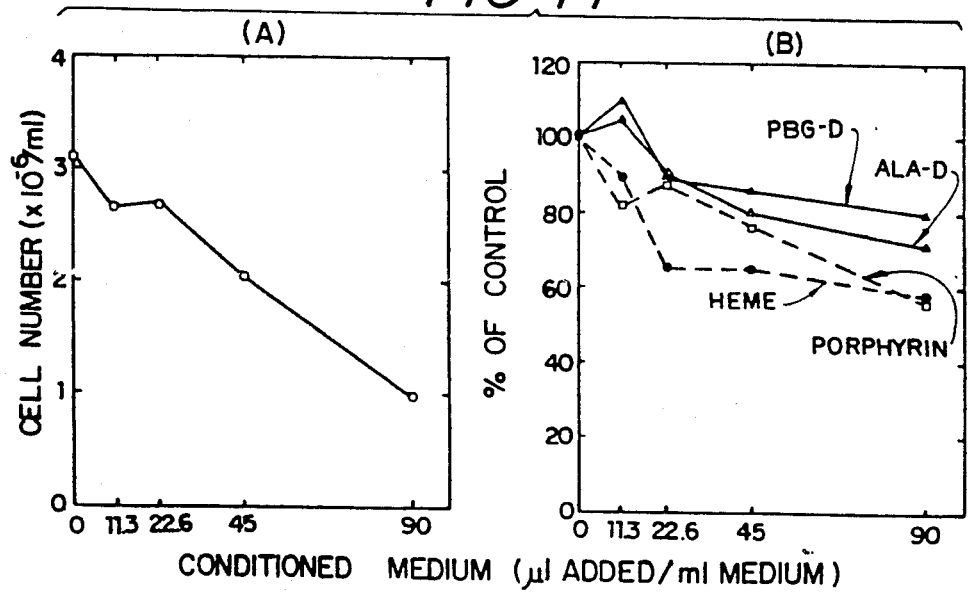

FIG. 11 shows the dose dependent effect of the endotoxin-stimulated macrophage mediator on cell growth and erythroid differentiation of $Me_2SO$-treated Friend cells. Cells were incubated for 96 hours in the presence of 1.5% $Me_2SO$ with increasing concentrations of the macrophage mediator. Assays of enzymes and intermediates were performed as described in Example III, infra. Data are the mean of duplicate determinations.

Figure 12:
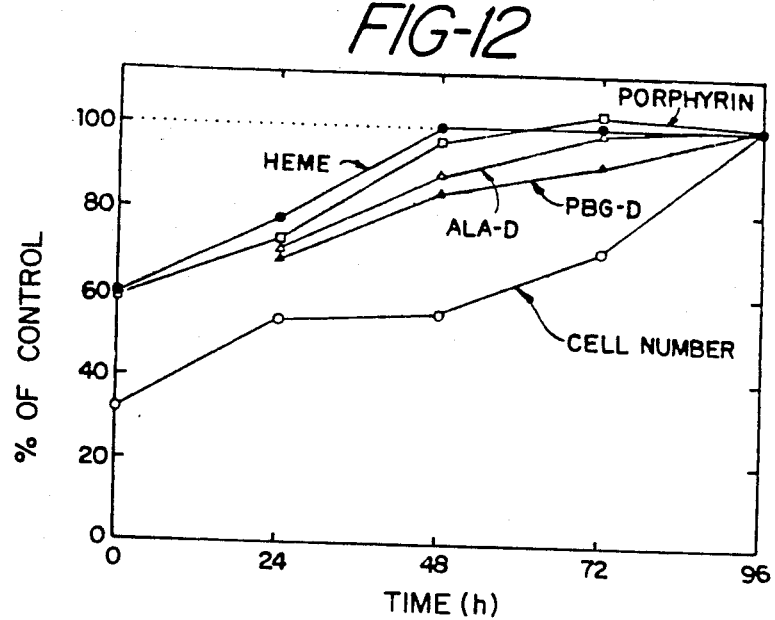

FIG. 12 shows the effect of delayed addition of the endotoxin-stimulated macrophage mediator on cell growth and erythroid differentiation.

Friend cells were incubated for 96 hours without changing the medium. $Me_2SO$ was added at time 0 to a final concentration of 1.5 vol %, while the endotoxin-stimulated macrophage mediator was added at the times indicated on the abscissa (80 μl conditioned medium per ml of growth medium). Cell number, activities of ALA dehydratase and PBG deaminase, heme and protoporphyrin contents were assayed at the end of incubation as described in Example III, infra. Data are the mean of duplicate determinations.

Values for control cultures treated with $Me_2SO$ alone were as follows:

| | |
|---|---|
| Cell number | $3.0 \ (\times 10^{-6}/ml)$ |
| ALA dehydratase | 3.00 (nmol PBG/$10^6$ cells, h) |
| PBG deaminase | 120 (pmol uroporphyrinogen/$10^6$ cells, h) |
| Protoporphyrin | 0.57 (pmol/$10^6$ cells) |
| Heme | 520 (pmol/$10^6$ cells) |

Figure 13:
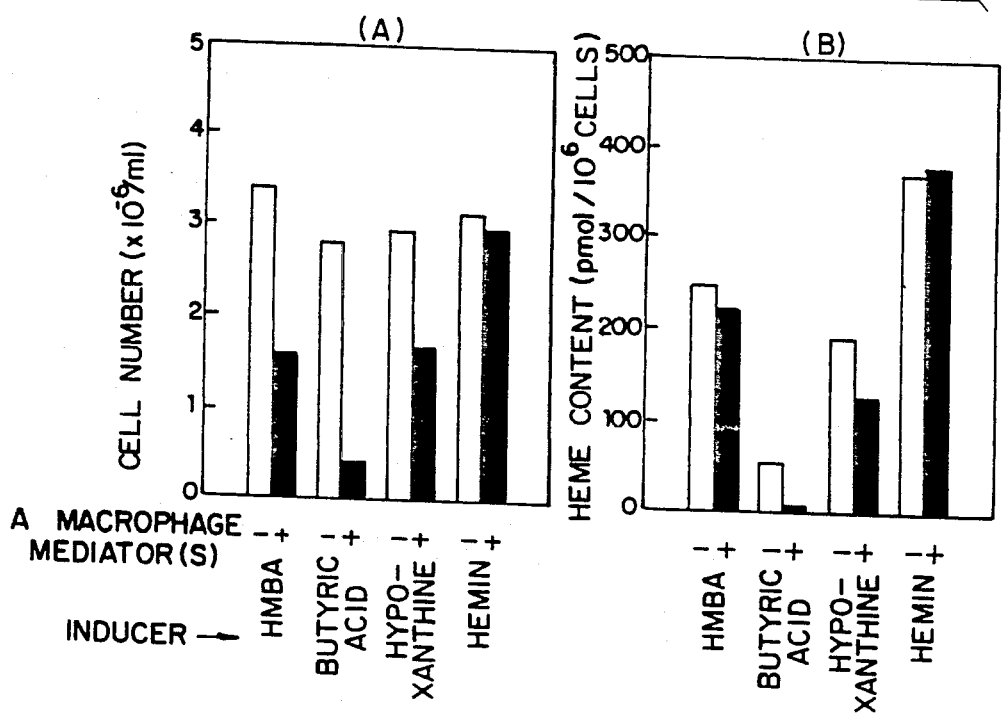

FIG. 13 shows the effect of the endotoxin-stimulated macrophage mediator on cell growth and heme content in Friend cells treated with HMBA, butyric acid, hypoxanthine or hemin.

Cells were incubated for 96 hours without changing the medium; inducing chemicals and the endotoxin-stimulated macrophage mediator (80 1 added/ml of growth medium) time 0. Final concentrations of chemicals were mM for HMBA, 1.3 mM for butyric acid, bmM for hypoxanthine and 0.1 mM for hemin. Assays were performed as described in Example III, infra. Data are the mean of duplicate determinations.

Figure 14:
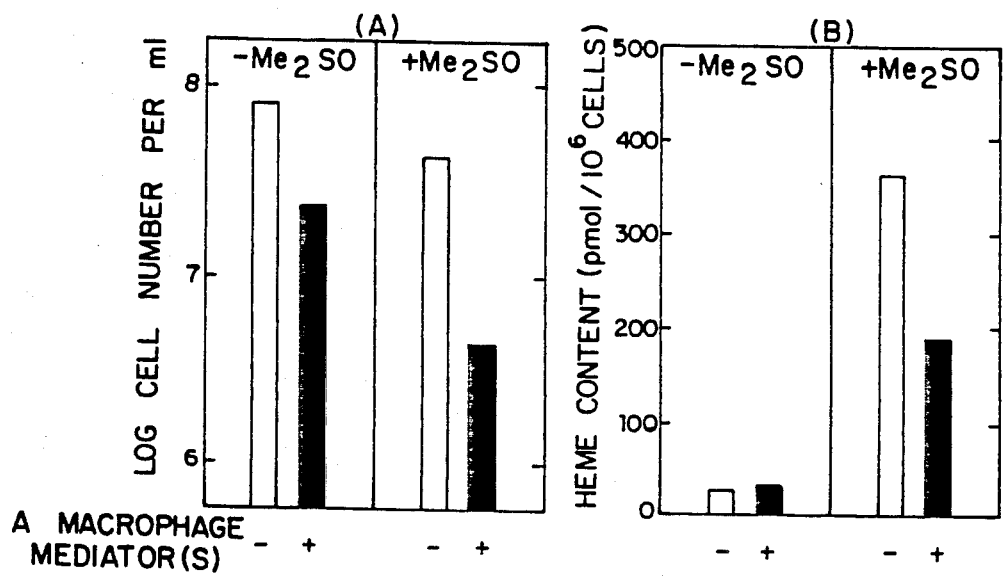

FIG. 14 shows the effect of endotoxin-stimulated macrophage mediator on the growth and differentiation of Friend cells growing at a constant rate.

DETAILED DESCRIPTION

As disclosed in our above referenced co-pending applications on this subject matter, we have discovered an agent which we identify herein as a mediator substance, that is produced by mammalian cells in response to stimulation by materials we refer to herein as stimulator materials, that characteristically accompany an invasive stimulus, such as bacteria, virus, some tumors, protozoa and other toxins such as endotoxemia. We have observed that the mediator substance causes the metabolism of certain of the cells of the mammal to switch from an anabolic state to a catabolic state. In particular, the mediator substance appears to suppress the activity of anabolic enzymes, such as lipoprotein lipase (LPL), and the other enzymes and inducing agents listed earlier herein. It is theorized that these mediator substance is part of a communications system in mammals, between the immune system and the energy storage tissues of the body. Thus, in response to various invasive stimuli in mammals, such as those listed before, it is theorized that the mediator substance is produced and exert an effect on energy storage tissue such as adipose tissue, muscle, the liver, and the like, of the impending need for energy to combat the invasion. More particularly, the mediator substance may cause these storage tissues to switch from an anabolic to a catabolic state, to facilitate the supply of such energy. If the invasion is of short duration, the mammal can quickly recover and replenish its energy stores; however, if the invasion is of a chronic nature, shock generally manifested by complete energy depletion, cachexia and death, can result.

During the initial work wherein the foregoing observations were made, the method for preparing the mediator was developed, and an illustrative preparation is set forth initially in Example I, in paragraph D, wherein peritoneal exudate cells were appropriately cultured and thereafter incubated in the presence of the known stimulator material endotoxin. After incubation, the macrophage cells are induced to produce the mediator substance. In one aspect, such inducement can occur over an extended incubation, i.e. on the order of 20 hours or more. The exact period for such incubation, however, may vary, and the invention is not limited to a specific time period.

Thereafter, the mediator substance may be recovered from the cell culture and stored for later use in one or more of the ways disclosed herein. Recovery may be effected by one of numerous well known techniques, including centrifugation and precipitation. For example, the culture described in paragraph D of Example I, was centrifuged and the supernatant thereafter drawn off. Alternately, the mediator may be precipitated either with a 40-60% solution of ammonium sulfate or by adsorption onto DEAE cellulose or like exchange resins. The choice of the particular method for recovery of the mediator substance is within the skill of the art.

The invention also relates to methods for detecting the presence of invasive stimuli in mammalian hosts by measuring the presence and activity of the mediator substance. As mentioned earlier, the mediator substance can be used to produce antibodies to themselves in rabbits, goats, sheep, chickens or other mammals, by a variety of known techniques, including the hydridoma technique utilizing, for example, fused mouse spleen lymphocytes and myeloma cells. The antibody can be isolated by standard techniques and utilized as a test for the presence of the mediator substance in the suspected mammalian hosts.

Further, the antibody or antibodies can be utilized in another species as though they were antigens, to raise further antibodies. Both types of antibodies can be used to determine the presence of mediator substance activity in the mammalian body, particularly in human serum, so as to determine the presence of invasive stimuli such as bacterial, viral, or protozoan infection, or the presence of certain tumors, and to follow the course of the disease. For purposes of the following explanation, the antibody or antibodies to mediator activity, will be referred to as $Ab_1$ the antibody or antibodies raised in another species will be identified as $Ab_2$.

The presence of mediator substance activity(ies) in the serum of patients suspected of harboring toxic levels thereof can be ascertained by the usual immunological procedures applicable to such determinations. A number of useful procedures are known. Three such procedures which are especially useful utilize either mediator labeled with a detectable label, antibody $Ab_1$ labeled with a detectable label, or antibody $Ab_2$ labeled with a detectable label. The procedures may be summarized by the following equations wherein the asterisk indicates that the particle is labeled, and "Med" stands for mediator activity:

A. $Med^* + Ab_1 = Med^*Ab_1$

B. $Med + Ab_1^* = MedAb_1^*$

C. $Med + Ab_1 + Ab^*_2 = Med\ Ab_1Ab_2^*$

The procedures and their application are all familiar to those skilled in the art and accordingly may be utilized interchangeably within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance the mediator substance forms a complex with one or more antibody(ies) and that one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_1$ may be raised in rabbits using a mediator as the antigen and $Ab_2$ may be raised in goats using $Ab_1$ as an antigen. $Ab_2$ therefore would be an anti-rabbit antibody raised in goats. For purposes of this description and claims, $Ab_1$ will be referred to as a mediator activity antibody and $Ab_2$ will be referred to as an antibody reactive with a mediator activity antibody or, in the alternative, an "anti-body".

The labels most commonly employed for these studies are radioactive elements, enzymes, chemicals which fluoresce when exposed to ultraviolet light, and others.

A number of fluorescent materials are known and can be utilized as labels. These include, for example fluorescein, rhodamine and auramine. A preferred detecting material is anti-rabbit antibody prepared in goats and conjugated with fluorescein through an isothiocyanate.

The mediator composition(s) can also be labeled with a radioactive element or with an enzyme. The radioactive label can be detected by any of the currently available counting procedures. The preferred isotope $^{14}C$, $^{131}I$, $^{3}H$, $^{125}I$ and $^{35}S$. The enzyme label can be detected by any of the presently utlized colorimetric spectrophotometric, fluorospectrophotometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galacetosidase, urease, glucose oxidase plus peroxidase, galactose oxidase plus peroxidase and acid phosphatase. U.S. Pat. Nos. 3,654,090; 3,850,752; 4,016,043; are referred to by way of example for their disclosure of alternate labeling material, and materials.

High levels of mediator activity in the mammalian body may be toxic to the mammal and cause irreversible shock. The antibody(ies) specific to a mediator is useful to treat hosts suffering from this metabolic derangement. The patient can be treated, for example, parenterally, with a shock-reducing, effective dose of the antibody to neutralize at least a portion of the mediator. The dose will, of course, vary in accordance with the factors well known and understood by the physician or veterinarian such as age, weight, general health of the patient and the concentration of the mediator.

In a further embodiment of this invention, commercial test kits suitable for use by a medical specialist may be prepared to determine the presence or absence of mediator substances in a suspected host. In accordance with the testing techniques discussed above, one class of such kits will contain at least the labeled mediator or its binding partner, an antibody specific thereto. Another which contain at least $Ab_1$ together with labeled $Ab_2$. Still another will contain at least $Ab_1$ and directions, of course, depending upon the method selected, e.g., "competitive", "sandwich", "DASP" and the like. The kits may also contain peripheral reagents such as buffers, stabilizers, etc.

Accordingly, test kits may be prepared with various components to detect the mediator substance in sera or aqueous media. A first kit may be prepared to comprise:
   (a) a predetermined amount of at least one labeled immuno-chemically reactive component obtained by the direct or indirect attachment of a mediator substance or a specific binding partner thereto to a detectable label;
   (b) other reagents; and
   (c) directions for use of said kit.

More specifically, a diagnostic test kit for the demonstration of a mammal's reaction to invasive stimuli may be prepared comprising:
   (a) a known amount of one mediator substance as described above (or its binding partner) generally bound to a solid phase to form a immunosorbent, or in the alternative, bound to a suitable tag,;
   (b) if necessary, other reagents; and
   (c) directions for use of said test kit.

Additional kits may be formulated to take advantage of numerous extant immunological protocols and techniques, and such modifications are considered within the scope of the invention.

In yet another aspect of the invention, antibodies specific to the aforementioned mediator may be administered in pharmaceutical compositions in response to shock produced by viruses, bacteria, protozoa, etc. These pharmaceutical compositions comprise:
   (a) a pharmaceutically effective amount of the antibody together with
   (b) a pharmaceutically acceptable carrier. With the aid of suitable liquids, the antibodies may be used in injection preparations in the form of solutions. These compositions may then be administered to a human in the above manner in shock-reducing amounts to dissipate, if not overcome, the effects of the invasion/shock.

As an adjunct to the development of antibodies and their use in the techniques described above, the present invention extends to methods of treatment of various conditions, such as shock, cachexia etc., that are found to exist as a result of undesirably high mediator substance activity in the mammalian host. In such instance, the method of treatment may include the detection of the presence and activity of the particular mediator substance, and the subsequent administration of the appropriate antibody or antibodies to the host, in amounts effective to neutralize the undesired mediator substance activity.

Conversely, certain adverse conditions in mammals such as obesity, may result from excess anabolic activity. For example, obesity may be caused by undesirably high levels of activity of the anabolic enzymes lipoprotein lipase, acetyl Coenzyme A carboxylase and fatty acid synthetase. The invention accordingly includes a method for treating obesity, comprising administering a mediator substance in an acceptable form, and in an amount effective to assist in restoring proper body weight. Administration of such treatment, however, would be under strict control by a physician, and the amount, manner and frequency of administration of the mediator would be carefully determined and constantly monitored.

In addition to treatment with antibodies raised by a mediator substances, the present invention includes an assay system, for the examination of potential substances, such as drugs, agents, etc. to inhibit the synthesis or activity of a mediator substance. As described earlier, appropriate cell cultures such as the 3T3-L1 and the Friend virus transformed erythroleukemia cells may be initially treated with a particular mediator to inhibit the activity of a particular anabolic actor, after which the potential drug etc. may be added, and the resulting cell culture observed to determine whether changes in the activity of the anabolic actor have taken place. While the foregoing description makes reference to specific cell cultures for the present assay, it is to be understood that the invention is not limited thereto.

Certain compounds have already been screened, to determine whether or not each inhibited mediator production and/or the effect of the mediator. Compounds tested and the results of such tests are set forth in the table, below.

TABLE

| Entity | Mediator Production | Mediator Effect |
|---|---|---|
| Dexamethasone $10^{-6}$ M | + | − |
| Aspirin $10^{-3}$ M | − | − |
| Indomethacin $10^{-5}$ | − | − |
| Nalaxone $10^{-5}$ M | − | − |
| Thyroid Releasing Factor $10^{-7}$ M | − | − | denotes yes; − denotes no)

As can be seen, only dexamethasone seems to have any effect. And even dexamethasone only has an effect on "mediator" production and, thus, is only effective at the beginning of the process. Once the mediator has been produced, the dexamethasone does not seem to have any further impact.

The following examples relate to the isolation of the mediator substance, and the observation of its activity, as related to certain anabolic enzymes, etc. A review of the following should lend greater appreciation to the origins and potentials of the present invention. Naturally, however, the specific materials and techniques may vary, as explained earlier, so that the following is presented as illustrative, but not restrictive of the present invention.

It should be noted that the terms "mediator" and "mediator substance", whether used in the singular or in the plural, are intended to refer to the same material that is isolated from macrophage cells that have been incubated with a stimulator material as disclosed herein, and both singular and plural usages of these terms, where present, should be viewed as equivalent for purposes of the present disclosure. At present, the exact composition of the mediator is unknown and, therefore, also unknown is whether the mediator is a single material or a mixture. Accordingly, the present terminology is intended to cover the "mediator" whether it is a single material or a mixture of materials. The term "mediator activity composition" and its plural may be distinct, as, although the mediator or mediator substance would be the same, the remainder of the composition may possibly vary depending upon the degree to which other cellular constituents, factors, etc. may be present therein.

EXAMPLE I

Isolation of Mediator Activity Compositions

A. Mice used in Testing: Male C3H/HeN endotoxin sensitive mice (7-10 wk: 18-25 g) were obtained from Charles River Breeding Laboratory (Wilmington, Mass.). Male C3H/HeJ, endotoxin-resistant mice (7-10 wk: 18-25 g) were obtained from The Jackson Laboratory (Bar Harbor, Maine). Mice were fed ad libitum on Rodent Laboratory Chow (Ralston Purina Co., St. Louis, Mo.) until they were utilized. The chow diet was removed 24 hours prior to each experiment and replaced with a solution of 25% sucrose in water. The animals, once injected, were only allowed access to water. Three to 10 C3H/HeN or C3H/HeJ mice were employed in each experimental group.

In conducting the various experiments, each mouse was injected intraperitoneally with one of the following: (i) 0.04 to 100 μg of endotoxin; (ii) 0.5 ml of serum obtained from C3H/HeN mice treated with endotoxin or saline; (iii) 1 ml of medium from cultures of peritoneal exudate cells of mice incubated in the presence or absence of endotoxin. Animals were sacrificed by decapitation.

B. Assay for Serum Triglyceride Concentration and Tissue Lipoprotein Lipase Activity: The triglyceride concentration was measured with an enzymatic assay (Triglyceride Test Set No. 961, Hycel Inc., Houston, Tex.). Lipoprotein lipase activity was assayed by the methods of Pykalisto, et al., PROC. SOC. EXP. BIOL. MED., 148 at 297 (1975); and Taskinen, et al., DIABETOLOGIA 17 at 351 (1979), both incorporated herein, with some modifications. Epididymal fat pads were excised immediately after the decapitation of each mouse. The tissues were rinsed in sterile Dulbecco's Modified Eagle medium (DME) (Gibco, Grand Island, N.Y.) containing 2% bovine serum albumin (fraction V, Reheis Chemical Company, Phoenix, Ariz.) and blotted on sterile filter paper. The tissues were minced with scissors, put into pre-weighed sterile polypropylene culture tubes (17×100 mm, Falcon Division of Becton, Dickinson and Company, Cockeysville, Md.) containing 1 ml of DME medium supplemented with 2% bovine serum albumin, and 2 U of heparin to release LPL (Lipo-Hepin, Riker Laboratories, Inc., Northridge, Calif.). Tubes with the tissues were sealed under 5% $CO_2$, balance air and incubated at room temperature with continuous gentle shaking. Tissue weight was determined by the difference of the weights of the tube before and after the addition of the tissue. Approximately 100–300 mg of tissue was removed and the activity of lipoprotein lipase released from the tissue was determined.

The enzyme assay was carried out by the method of Nilsson-Ehle and Shotz, J. LIPID. RES. 17 at 536 (1976), incorporated herein, with minor modifications. The samples were incubated at 37° C. for 90 minutes of incubation. Each sample was assayed in duplicate. One milliunit of the enzyme activity was defined as one nanomole of free fatty acid released per minute. The enzyme activity released per gram of wet tissue was compared between experimental groups and control groups of each study since there was considerable variation of LPL activity day to day. In order to compare the data between experiments, the data was expressed as percent of the average activity of the control group. The range observed in C3H/HeN mice was from 32 to 59 mU/g for adipose tissue. Values to 31 of 172 mU/g for adipose tissue were observed in C3H/HeJ mice.

C. Collection of Serum for Endotoxin Treated Mice:

Blood was obtained under sterile conditions from the axillary pit of C3H/HeN mice 2 hours after i.p. injection of endotoxin (either 2 or 100 μg/mouse) in 0.1 ml of saline or saline alone. Serum was prepared within one hour after bleeding and either used immediately or kept at 80° C. until use.

D. Preparation of Endotoxin Treated Peritoneal Exudative Cells: Peritoneal exudate cells were obtained by peritoneal lavage with pyrogen-free saline (Abbott Laboratories, North Chicago, Ill.) from C3H/HeN mice (25–33 g). These mice were injected i.p. 6 days prior to lavage with 3 ml of sterile Brewer's thioglycollate medium (Difco Laboratories, Detroit, Mich.) to increase cell production. The peritoneal exudate cells obtained by this procedure consist of approximately 60% macrophages, 20% small lymphocytes, 15% large lymphocytes, and 5% eosinophils.

The exudate cells ($2 \times 10^6$ cells/well) were incubated in serum-free RPMI-1640 medium (Gibco, Grand Island, N.Y.) in culture plates containing 4.5 cm² wells at 37° C. in 5% $CO_2$. After 3 hours, the cultures were washed three times with the medium to remove nonadherent cells. The cells which adhered to the dish were mainly macrophages. In the various testing procedures, the cells were incubated in serum-free RPMI-1640 medium in the presence or absence of endotoxin (10 μg/ml). The culture medium was removed at 26 hours incubation and centrifuged at 1000 g for 5 minutes at 4° C. The supernatant was used for testing immediately or kept at −80° C. until required for testing. No difference in activity was noted after storage for one month under these conditions.

The various studies and isolation procedures will now be described.

E. Mediator Activity Produced in Mice: The LPL activity from adipose tissue and the serum triglyceride concentration of endotoxin-sensitive mice which had been injected with either saline (controls or 100 μg of endotoxin) 16 hours before sacrifice was observed. This amount of endotoxin corresponds in this strain of mice to a dose in which half the animals die within three days after injection. It was observed that the LPL activity of adipose tissue in the endotoxin-treated animals was depressed to 4.5% of the control values while the triglyceride concentration in the serum of the endotoxin treated animals were elevated 2.6 times that of control animals.

The fact that the lowering of LPL activity is to be attributed to mediator activity produced as a result of stimulation by endotoxin and not to the endotoxin itself is supported by the results obtained when the serum from endotoxin-sensitive mice which had been treated with 100 μg of endotoxin 2 hours prior to bleeding was injected into another group of endotoxin-sensitive mice. For this test, the control group was injected with serum obtained from another group of endotoxin-sensitive mice which had been injected with pyrogen-free saline. LPL activity in epididymal fat pads were measured 16 hours later.

Figure 1A:
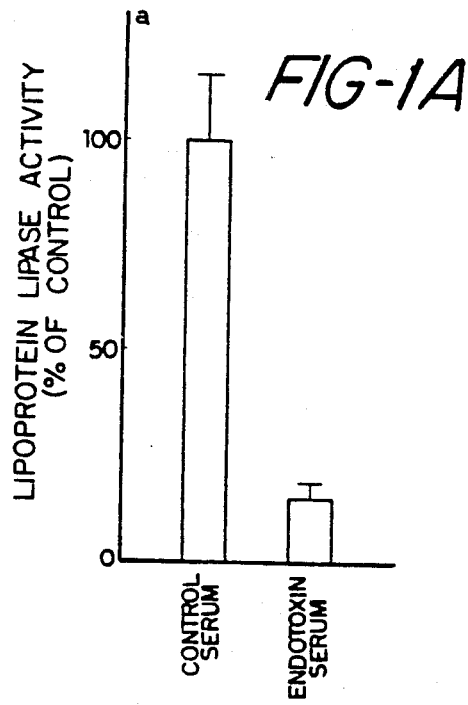
FIG. 1A shows the effect of serum from endotoxin-sensitive mice treated with endotoxin on adipose tissue LPL activity in endotoxin-sensitive mice. Mediator activity was observed and conclusions drawn as set forth in Example 1, paragraph E herein. The data are expressed as the mean ($\pm$SEM) of six animals for each group.

As further illustrated in FIG. 1A, the serum from endotoxin-treated mice markedly suppressed LPL activity in these animals compared to the activity in the control group of animals. Since greater than 90% of endotoxin is known to be cleared from circulation in 15 minutes, it is clear that the observed effect on LPL activity is not due to a direct effect on any remaining endotoxin present in the serum 2 hours after injection. It must be caused by a humoral factor or mediator produced as a result of the endotoxin injection.

Figure 1B:
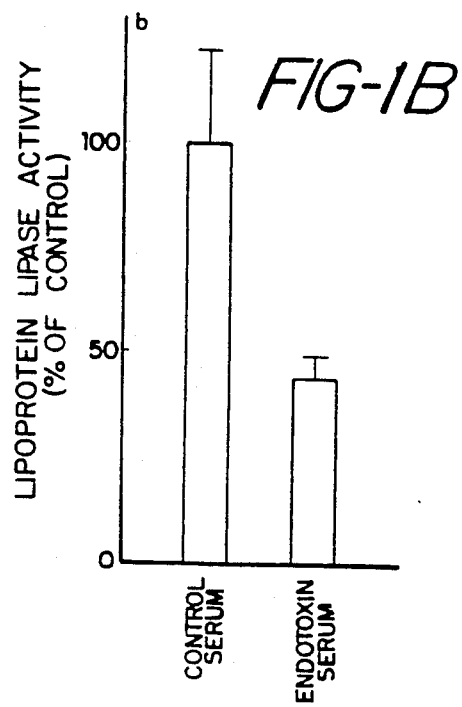
FIG. 1B shows the effect of serum from endotoxin-sensitive mice treated with endotoxin on adipose tissue LPL activity in endotoxin-resistant mice. The data are expressed as the mean ($\pm$SEM) of three animals for each group.

To further exclude direct endotoxin effects, serum obtained from the sensitive C3H/HeN strain of mice which had been injected 2 hours previously with a smaller amount (2 μg) of endotoxin was injected into endotoxin-resistant C3H/HeJ mice. The LPL activity of adipose tissue was measured 16 hours after the injection to minimize the possibility of direct endotoxin effect and revealed a 55-percent decrease of LPL activity as illustrated in FIG. 1B. Since resistant animals do not respond to this small amount of endotoxin, this observation again establishes that a humoral mediator is involved to which the resistant mice are capable of responding.

Figure 2:
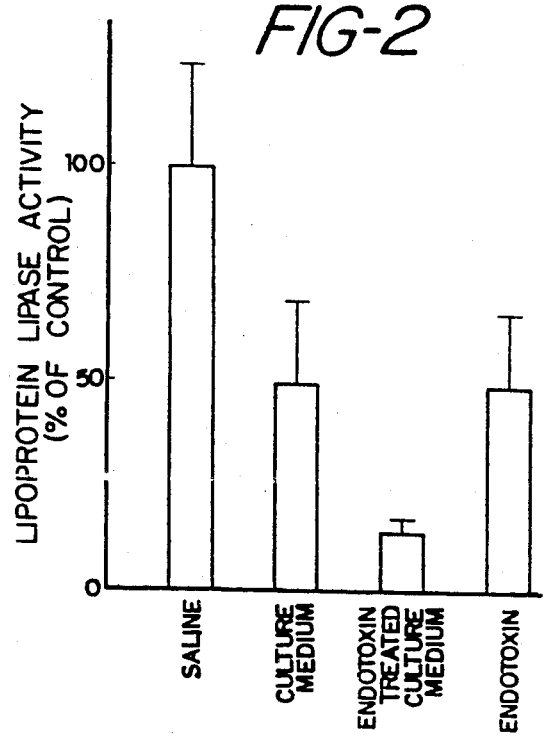
FIG. 2 shows the effect of medium from exudate cell cultures on adipose tissue LPL in endotoxin-resistant mice. The data are presented as the mean ($\pm$SEM) of four or five animals.

F. Mediator Activity Produced in Mice Peritoneal Exudate Cells: Experiments were undertaken to show that exudate cells could be stimulated to produce the mediator by which endotoxin suppresses the LPL activity of adipose tissue. Exudate cells were obtained from endotoxin-sensitive (C3H/HeN) mice by peritoneal lavage. These cells were incubated in vitro in the presence of 10 μg/ml or absence of endotoxin. One ml of the media from these cell cultures was injected into the endotoxin-resistant strain of C3H/HeJ mice. As displayed in FIG. 2, the average LPL activity in adipose tissue of animals injected with medium from the exudate cells incubated with endotoxin was 32% of that of mice which received either medium from cell cultures without added endotoxin or medium containing endotoxin but without cells. The difference in enzyme activity between animals treated with medium from endotoxin treated cell cultures and those animals treated with saline alone was much greater than the other controls, suggesting that a small amount of mediator was released by exudate cells in the absence of endotoxin and that the small amount of endotoxin in the medium without cells was enough to partially lower LPL activity.

From the above, it is clear that endotoxin administration markedly suppresses adipose tissue LPL in genetic strains of mice which are sensitive to endotoxin shock and death. This action is mediated by humoral factor or factors which can suppress adipose tissue LPL in mice not sensitive to endotoxin shock, as well as in mice which are sensitive. Peritoneal exudate cells sensitive to endotoxin are also capable of producing this humoral mediator.

G. Isolation of Mediator Activity Compositions from Mouse Peritoneal Exudate Cells: Culture medium is collected from mouse peritoneal exudate cells cultured in RPMI-1640 growth medium exposed to 10 μg/ml of endotoxin for 24 to 36 hours and centrifuged at 500 rpm for 10 minutes at 4° C. The supernatant is subjected to ultrafiltration through an Amicon PM-10 membrane with a 10,000-Dalton cut-off. The volume of the retentate is concentrated by filtration to approximately 7 ml, placed on a Sephacryl 300 column (1.695 cm) and eluted with phosphate-buffered saline (PBS) (pH 7.4) at 4 ml/hr and 4° C. The volume of each collected fraction was 3.6 ml. The fractions were analyzed for LPL activity. Fractions eluting at 108 to 115 ml and 133 to 140 ml were found to be active in the LPL assay. The molecular weights of the mediator active compositions in these fractions are about 300,000 and 70,000 Daltons, respectively.

The lyophylized filtrate from the ultrafiltration is dissolved in a minimal amount of distilled water, chromatographed on a Sephadex G 50 column (1.6×95 cm), and eluted with PBS (pH 7.4) at a flow rate of 6 ml/hr. Fractions of 3 ml were collected and analyzed for LPL activity. The activity was located in fractions eluting at 170 to 179 ml which corresponds to a molecular weight to about 400 to 1,000 Daltons.

The approximate molecular weights were determined in accordance with standard practice by comparison with proteins of known molecular weight. The standards employed were ferritin, molecular weight—440,000 Daltons; bovine serum albumin, molecular weight—68,000; carbonic anhydrase, molecular weight—30,000; and ribonuclease, molecular weight—17,000; all in Daltons. As is known to those skilled in the art, molecular weights determined by this procedure are accurate to about 20%.

Mediator activity compositions can also be isolated from mouse peritoneal exudate cells by vacuum dialysis using a Millex membrane (Millipore Corporation, Bedford, Mass.) according to the following procedure.

Vacuum dialysis was carried out in dialysis tubing with molecular weight cut-offs at 13,000–14,000 Daltons. Samples of conditioned medium obtained from endotoxin-treated exudate cell cultures were placed under vacuum for 6 hours at 4° C. with a 40-percent reduction in volume. Aliquots from inside and outside the bag were assayed for mediator activity.

It was found that all of the activity was retained during vacuum dialysis with membranes having a 12,000-Dalton pore cutoff. The mediator composition isolated by this procedure, therefore, has a molecular weight greater than 12,000 Daltons. This composition contains the two higher molecular weight compositions previously described. The reason that the lowest molecular weight composition is not obtained is not clear. Possibly because it is absorbed in the Millex membrane or because the procedure with the Amicon filter is more rapid.

The stability of the various mediator compositions to heat was assessed by heating at 100° C. for 15 minutes. The inhibitory effect of the mediators on the lipoprotein lipase was completely abolished by this treatment.

To determine whether the mediators are intracellular constituents of nontreated cells, exudate cells were sonicated and the extract was assayed for mediator activity. These extracts had no measurable mediator. The mediators, therefore, are not a normal intracellular substance of exudate cells, but are synthesized or processed in these cells following stimulation by endotoxin.

The fact that the mediator activity compositions are in the tissue culture medium of tissue cultures of peritoneal exudate cells make it clear that they are water-soluble.

The mediators, therefore, are capable of reducing LPL activity in the mammalian body, can be isolated by standard procedures such as chromatography, dialysis and gel electrophoresis from the serum of endotoxin-treated animals or from a cell culture of peritoneal exudate cells incubated with endotoxin.

H. Studies of 3T3-L1 Preadipocytes: The properties of the mediator compositions were further investigated using the well defined 3T3-L1 "preadipocyte" model system, by the inventors herein and co-workers, P. Pekala and M. D. Lane. 3T3-L1 preadipocytes, originally cloned from mouse embryo fibroblasts, differentiate in monolayer culture into cells having the biochemical and morphological characteristics of adipocytes. During adipocyte conversion, 3T3-L1 cells exhibit a coordinate rise in the enzyme of de novo fatty acid synthesis and triacylglycerol synthesis. Similarly, the activity of lipoprotein lipase, another key enzyme of lipid metabolism, rises 80–180 fold during adipose conversion. The activity of the enzyme is enhanced by the presence of insulin in the medium and appears to be similar to the lipoprotein lipase of adipose tissue.

Utilizing cells of the 3T3-L1 preadipocyte cell line, it was found that addition of the mediator compositions, derived from mouse peritoneal exudate cells exposed to endotoxin as described above, suppresses the activity of lipoprotein lipase.

The endotoxin used in the 3T3-L1 cell culture study was obtained as described above. Cell culture media and fetal calf serum were obtained from Gibco Laboratories (Long Island, N.Y.). 3-isobutyl-1-methylxanthine was from Aldrich Chemical (Milwaukee, Wis.), dexamethasone from Sigma Chemical Company (St. Louis, Mo.), and insulin from Eli Lilly Corporation (Arlington Heights, Ill.). Triolein was from Nu Check Prep, Inc. (Elysian, Minn.). Crystalline bovine serum albumin was from Calbiochem-Behring Corporation (LaJolla, Calif.).

I. 3T3-L1 Cell Culture: 3T3-L1 preadipocytes were cultured as previously described [MacKall, et al., J. BIOL. CHEM. 251 at 6462 (1976), and A. K. Student, et al., J. BIOL. CHEM., 255 at 4745–4750 (1980)] in Dulbecco's modified Eagle's medium (DME medium) containing 10% fetal calf serum. Differentiation leading to the adipocyte phenotype was induced by the Student, et al., modification of the method of Rubin, et al., [J. BIOL. CHEM. 253 at 7570–7578 (1978)]. Two days after confluence, the medium was supplemented with 0.5 mM isobutyl-methylxanthine, 1 $\mu$M dexamethasone and 10 $\mu$g of insulin per ml. Forty-eight hours later, the medium containing isobutyl-methylxanthine, dexamethasone, and insulin was withdrawn and replaced with medium containing insulin at a reduced concentration of 50 ng per ml.

J. Effect of Mediator Compositions on 3T3-L1 Cells: One hour after the culture medium was replaced with medium containing the reduced concentration of insulin, conditioned media from cultured exudate cells with or without added endotoxin were added to 3T3-L1 cell cultures. Incubation of the cells with the conditioned medium was carried out for up to 20 hours. At indicated times, the amount of lipoprotein lipase activity was measured in three compartments: (1) the activity of the medium; (2) the activity released from the cells following incubation with heparin (this activity represents the enzyme associated with the outer surface of the cell membrane); and (3) intracellular activity.

Following the withdrawal of the medium, the dishes were rinsed once with fresh medium and the lipoprotein lipase associated with the cell membrane was released by incubation for one hour in DME medium supplemented with heparin (10 U/ml) and insulin (50 ng/ml). After removing this medium, the dishes were rinsed with PBS and the cells were scraped into 1 ml of 50 mM, $NH_3/NH_4Cl$ buffer, pH 8.1 containing heparin 3U/ml. The cell suspension was sonicated (on ice) for 15 seconds and centrifuged at 500×g for 5 minutes. The supernatant was assayed for lipoprotein lipase.

Lipoprotein lipase assays were performed within 30 minutes after the preparation of each sample in duplicate by the method of Nilsson-Ehle and Shotz [J. LIPID. RES. 17 at 536–541 (1976)] with minor modifications. Briefly, 75 $\mu$l of enzyme was mixed with 25 $\mu$l of substrate containing 22.7 mM[3H]-triolein (1.4 uCi per mole), 2.5 mg per ml of lecithin, 40 mg per ml bovine serum albumin, 33% (V/V) human serum and 33% (V/V) glycerol in 0.27M Tris-HCl, pH 8.1, and incubated at 37° C. for 90 minutes. One milliunit of enzyme activity was defined as the release of one nanomole of fatty acid per minute. The lipase activity in all three compartments was inhibited >90% by addition of 1M NaCl and >80% by omission of serum which is the source of apolipoprotein C-II needed for enzymatic activity.

To test the effect of the mediator on the lipoprotein lipase activity of 3T3-L1 cells, the conditioned medium obtained from mouse peritoneal exudate cells cultured in the presence or absence of endotoxin, was added to 3T3-L1 cells in monolayer culture. After a 20-hour incubation at 37° C., lipoprotein lipase activity was assessed in three compartments: (1) the culture medium; (2) the cell surface (heparin-releasable lipase activity) and; (3) the intracellular fraction.

Figure 3:
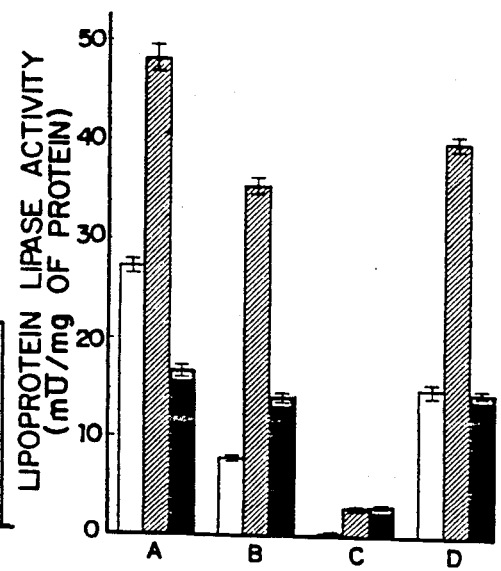
FIG. 3 shows the effect of conditioned medium from endotoxin-treated mouse peritoneal exudate cells over lipoprotein lipase activity of 3T3-L1 cells. Data are expressed as mean SEM (n=4).
Figure 5A:
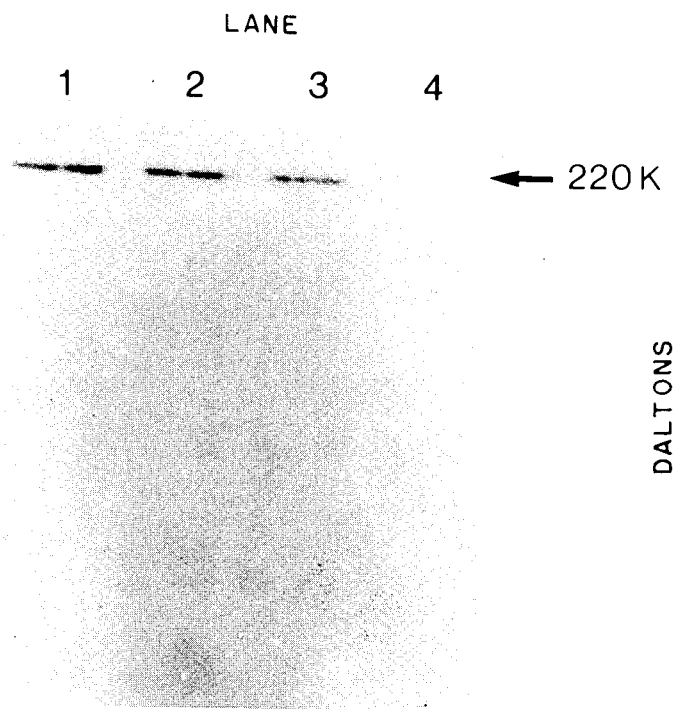
FIG. 5 shows the effect of mediator that suppresses the synthesis of acetyl CoA carboxylase. At the indicated times after exposure of the 3T3-L1 cells to the mediator (300 $\mu$l of conditioned medium, the cells were pulse-labeled with 0.5 mCi of $^{35}$S-methionine for 1 hour. Cytosolic fractions were obtained by digitonin treatment of a monolayer. Aliquots of the cytosolic fractions ($2 \times 10^5$ cpm for all determinations) were incubated with anti-acetyl CoA carboxylase and the immunoprecipitable material isolated and characterized as described in Example II, infra. Panel A: Autoradiogram of a 7.5%-acrylamide-0.1% SDS gel analysis of immunoadsorbable protein. Lane 1—control, without exposure to mediator; Lanes 2, 3, and 4—exposure of the cells to the mediator for 3, 6 and 20 hours, respectively. Panel B: Results of a densitometric scan of the autoradiogram, indicating percent of immunoadsorbable material remaining relative to control, after exposure to the mediator.
Figure 5B:
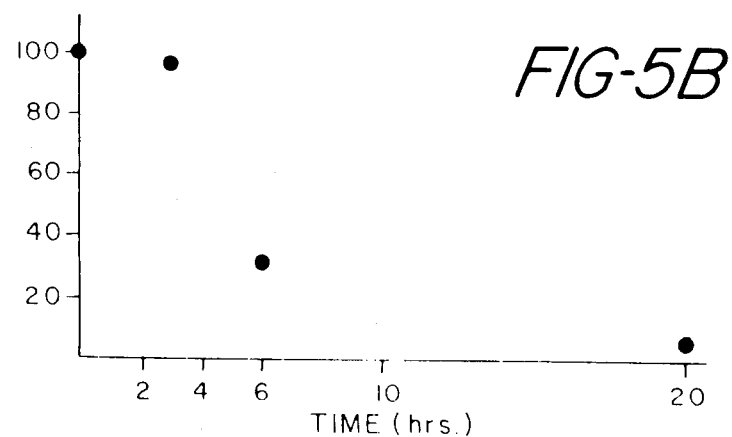
Figure 7:
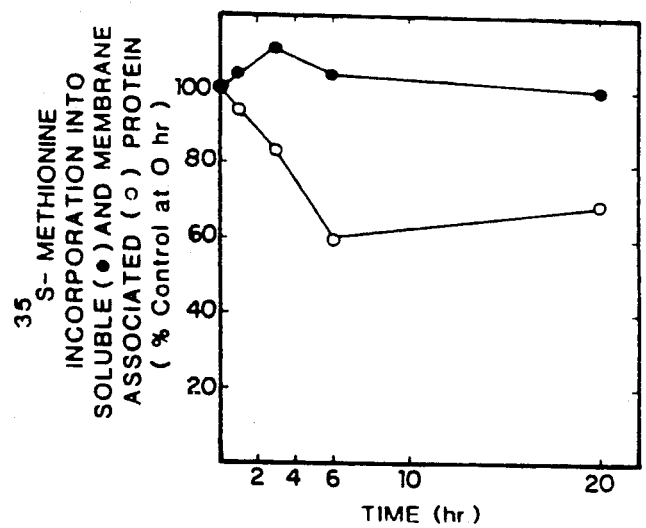
FIG. 7 shows the effect of the mediator on $^{35}$S-methionine incorporation into protein. 3T3-L1 cells were incubated with 300 $\mu$l of conditioned medium from endotoxin-treated mouse peritoneal exudate cells for the appropriate period and protein pulse-labeled with 0.5 mCi of $^{35}$S-methionine for 1 hour. Soluble proteins were obtained by digitonin treatment of the cells, the remainder of the monolayer was extracted with NP-40 and a membrane protein fraction obtained. Incorporation of $^{35}$S-methionine into acid precipitable material was determined as described in Example II, infra. The incorporation of radioactivity into soluble protein (●) or membrane protein (o) following exposure of the cells to the mediator are shown for the indicated time.
Figure 8:
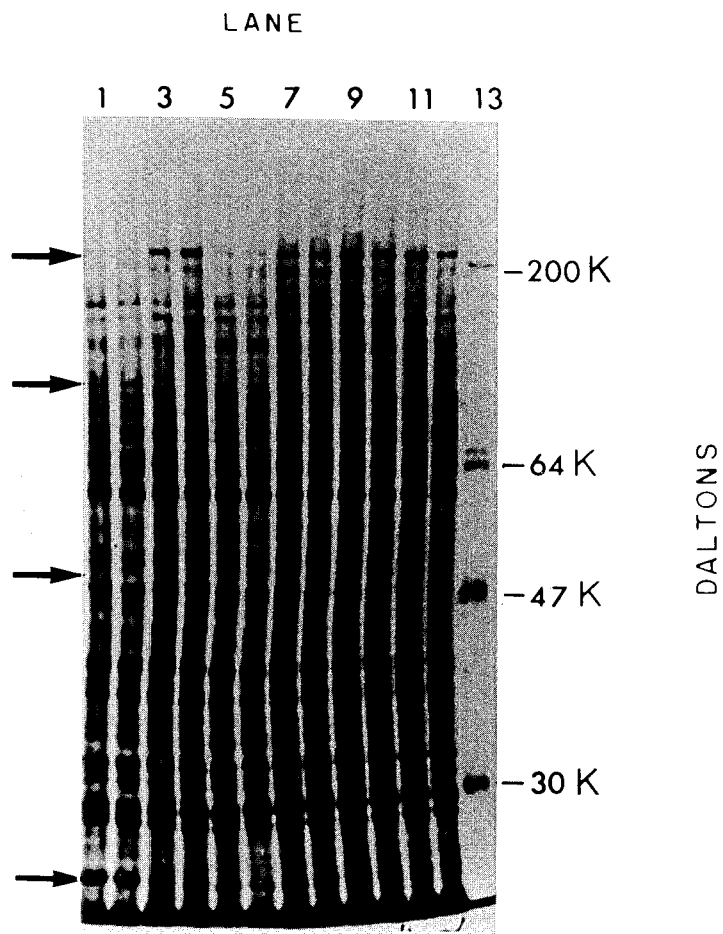
FIG. 8 shows the effect of mediator on protein synthesis in the cytosolic fraction of the cells. Autoradiogram of a 7.5%-acrylamide-0.1% SDS gel analysis of $^{35}$S-methionine labeled cytosolic protein after exposure of the cells of the mediator. 3T3-L1 cells were pulse labeled and the soluble protein was obtained by digitonin as described in Example II. Aliquots ($2 \times 10^5$ cpm) of the cytosolic fraction for each time point were applied to the gel and electrophoresed. Lanes 1 and 2, control without exposure to mediator; Lanes 3 and 4, 1 hour exposure to the mediator; Lanes 5 and 6, 3 hours of exposure; Lanes 7 and 8, 6 hours of exposure; Lanes 9 and 10, 20 hours of exposure to conditioned medium from mouse peritoneal exudate cells not exposed to endotoxin; Lanes 11 and 12, exposure of cells to mediator for 20 hours.
Figure 9:
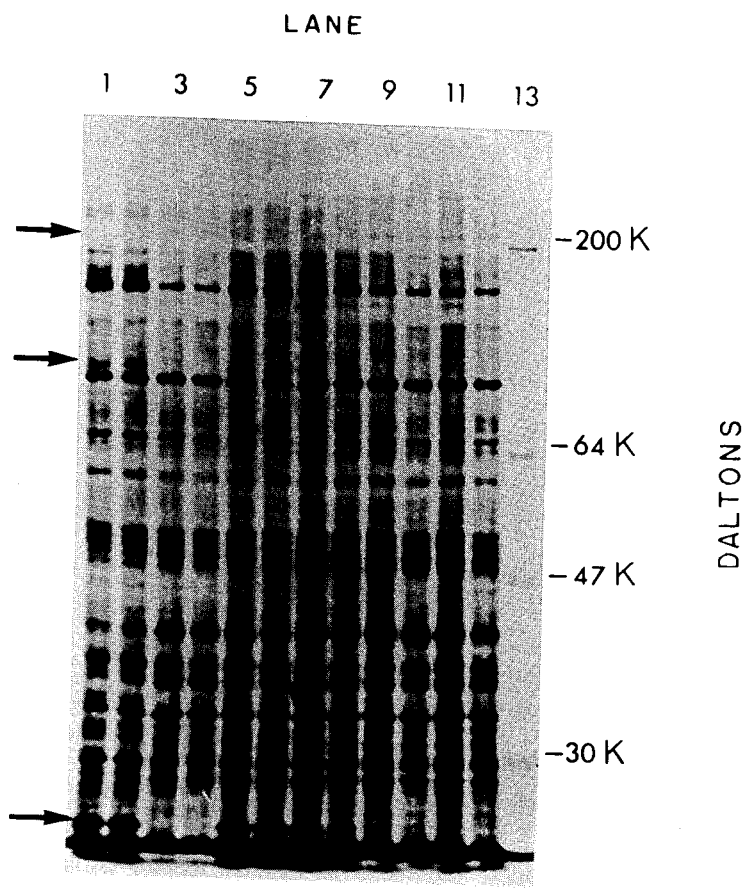
FIG. 9 shows the effect of mediator on protein synthesis in the membrane fraction of the cells. Autoradiogram of a 7.5%-acrylamide-0.1% SDS gel analysis of $^{35}$S-methionine labeled membrane protein after exposure of the cells to the mediator. Expreimental design was identical to that described in the legend to FIG. 8. Membrane proteins were obtained by NP-40 extraction as described in Example II. Lanes 1 and 2—control, without exposure to mediator; Lanes 3 and 4, 1 hour of exposure to the mediator; Lanes 5 and 6, 3 hours of exposure; Lanes 7 and 8, 6 hours of exposure; Lanes 9 and 10, 20 hours of exposure of the cells to conditioned medium from mouse peritoneal exudate cells not exposed to endotoxin; Lanes 11 and 12, exposure to mediator for 20 hours.

As shown in FIG. 3, Cols. A & C, the addition of media containing the mediator substance from endotoxin-stimulated exudate cells, markedly suppressed the lipoprotein lipase activity in all three compartments. The enzyme activities in the medium, on the cell surface (heparin releasable), and in the intracellular compartment were 0.1%, 6%, and 18%, respectively, of that of the control cells incubated with the same amount of fresh RPMI-1640 medium. No difference in morphology or extent of adipocyte conversion was detected between cells in the experimental and control groups. At the beginning of the study, approximately 20% of the cells exhibited triglyceride accumulation in the cytoplasm; 20 hours later, approximately 50% of both the experimental and control cells had accumulated triglyceride.

The medium from the culture of exudate cells not treated with endotoxin had little effect on the lipoprotein lipase activity of 3T3-L1 cells. While the medium from untreated exudate cells elicited some inhibition in the study shown in FIG. 3, Col. B in other similar studies, medium prepared identically had no inhibitory effect. Endotoxin itself also had a negligible inhibitory effect on lipoprotein lipase activity when the amount added was equivalent to that which might remain in the conditioned medium from endotoxin-treated exudate cells; a 19%, 9%, and 0% decrease was observed on medium, heparin-releasable and intracellular compartments, respectively. The decrease was greater (45% in medium, 17% in heparin-releasable, and 11% in the cells) when larger amounts (4.5 times) of endotoxin was employed, as shown in FIG. 3, Column D.

A possible explanation for the decreased activity of lipoprotein lipase described above is a direct inhibitory effect of mediators on the enzyme. This was examined by incubating medium from 3T3-L1 cell cultures which contained lipoprotein lipase with conditioned medium from cultures of endotoxin-treated exudate cells. It was found that the enzyme activity was not inhibited by the mediator compositions (103% of the control) at the time of mixing, and the rate of decay of enzyme activity was the same in the experimental group and the control group. Endotoxin also had no effect on the activity of lipoprotein lipase. The results imply that the mediator compositions depress lipoprotein lipase activity in 3T3-L1 cells by inhibiting the intracellular synthesis or processing of the enzyme.

The relationship between the amount of mediator compositions and lipoprotein lipase activity of 3T3-L1 cells was examined by incubating the cells with increasing amounts of the conditioned medium from endotoxin-treated exudate cells for 20 hours at 37° C. Ten $\mu$l of conditioned media according to 1.5 ml of culture media was sufficient to cause a substantial decrease in lipoprotein lipase activity, i.e., 57% decrease in the medium, 40% decrease in the heparin-releasable compartment, and 8% decrease in the cells. Enzyme activity was further depressed by increasing the amount of mediator containing medium. When 250 $\mu$l were added, a decrease of greater than 95% was observed in all three compartments. The amount of mediator present in conditioned medium varied somewhat from preparation to preparation.

The rate at which lipoprotein lipase activity declines after the addition of the mediators was also investigated. Conditioned medium containing mediators was added at selected intervals, and lipoprotein lipase activity was measured. A reduction of lipase activity was apparent as early as 30 minutes after addition of 3T-3L1 cells. Approximately half of the intracellular enzyme activity was lost after 2.5 hours. After 5 hours of incubation with a mediator, a maximal effect was observed. The amount of enzyme activity in the medium and that on the cell surface were also observed to decrease with a similar time course (data not shown).

The rapid decrease in lipoprotein lipase activity might reflect a competition with insulin since removal of insulin has been shown to lead to a rapid decline in lipoprotein lipase activity in 3T3-L1 cells. However, an attempt was made to reverse the suppressive effect of the mediator by increasing the concentration of insulin in the medium was not successful. For this study, the effect of incubating 3T3-L1 cells with media containing insulin at various concentrations (50 ng/ml to 50 $\mu$g/ml) and mediator was assessed for lipoprotein lipase activity. It was found that the inhibitory effect of the mediator on enzyme activity was not changed with increasing insulin concentrations. Even at an insulin concentration 1,000 greater (50 g/ml) than that of standard conditions (50 ng/ml), the inhibition was not reversed.

EXAMPLE II

Reasoning that other anabolic activities of the 3T3-L1 cells might be inhibited by the mediator, we studied two key enzymes: (1) acetyl CoA carboxylase; and (2) fatty acid synthetase; for de novo fatty acid biosynthesis. The following example based upon a manuscript in preparation by the inventors herein and coworkers, P. Pekala, M. D. Lane and C. W. Angus, presents evidence that the synthesis of these enzymes are also inhibited by the addition of the macrophage mediator. The results implicate a larger role for the mediator(s) and point to the presence of a communication system between immune cells and energy storage cells of mammals. Presumably, during invasion the immune cells can function as an endocrine system and selectivity mobilize energy supplies to combat the invasion.

A. Materials: Endotoxin (lipopolysaccharide) from *E. coli* 0127: B8 isolated by the method of Westphal, described supra, was purchased from Difco Laboratories (Detroit, Mich.). Cell culture media and fetal calf serum were obtained from Gibco Laboratories (Grand Island, N.Y.). 3-isobutyl-1-methylxanthine was from Aldrich Chemical (Milwaukee, Wis.); dexamethasone, from Sigma Chemical Company (St. Louis, Miss.); and insulin from Eli Lilly (Indianapolis, Ind.). IgG-SORB was from the Enzyme Center, Inc., (Boston, Mass.). L-[$^{35}$S]Methionine (800–1440 Ci/mmol) was from Amersham,. En$^3$Hance was obtained from NEN, (Boston, Mass.). Antiserum to fatty acid synthetase was kindly provided by Dr. Fasal Ashmad of the Papanicolau Cancer Research Institute, Miami, Fla.

B. 3T3-L1 Cell Culture: 3T3-L1 preadipocytes were cultured as previously described, [MacKall, et al., J. BIOL. CHEM. 251 at 6462 (1976)] in Dulbecco's modified Eagle's medium (DME medium) containing 10% fetal calf serum. Differentiation leading to the adipocyte phenotype was induced by the Student, et al., modification (A. K. Student, et al., J. BIO. CHEM. 255 at 4745–4750 (1980)) of the method of Rubin, et al., J. BIOL. CHEM. 253 at 7570 (1978). Two days after confluence, the medium was supplemented with 0.5 mM isobutyl-methylxanthine, 1 μM dexamethasone and 10 μg of insulin per ml. Forty-eight hours later, the medium containing isobutyl-methylxanthine, dexamethasone, and insulin was withdrawn and replaced with medium containing insulin at a reduced concentration of 50 ng per ml.

C. Preparation of Peritoneal Exudative Cells and Mediator Substances: Peritoneal exudate cells were obtained by peritoneal lavage from C3H/HeN mice (25–33 g; Charles River Breeding Laboratories, Wilmington, Mass.) which had been injected intraperitoneally with sterile Brewer's thioglycollate medium (Difco Laboratories, Detroit, Mich.; 3 ml per mouse) 6 days prior to harvest. The exudate cells obtained using this procedure are primarily macrophages with some contaminating lymphocytes, The cells ($4 \times 10^5$ cells per cm$^{2d}$) were incubated in serum-free RPMI-1640 medium for 3 hours after which nonadherent cells were removed by washing 3 times with medium. Cells adhering to the dish were primarily macrophages. These cells were further incubated in serum-free RPMI-1640 medium in the presence or absence of 10 g per ml of endotoxin. After 24 hours, the culture medium was removed and centrifuged at $1,000 \times g$ for 5 minutes at 4° C. The supernatant of conditioned medium obtained from cells exposed to endotoxin was assayed and found to contain the mediator substance that lowers LPL in 3T3-L1 cells. No difference in activity was noted after storage of the conditioned medium for one month at −80° C.

D. Effect of Mediator on 3T3-L1 Cells: One hour after the culture medium was replaced with medium containing the reduced concentration of insulin, conditioned media from cultured exudate cells with or without added endotoxin were added to 3T3-L1 cell cultures. Incubation of the cells with the conditioned medium was carried out for up to 20 hours.

E. Labeling of Cellular Proteins: A 6-cm plate containing induced 3T3-L1 cells was washed twice with 5 ml of methionine-free medium and incubated for 1 hour with 2 ml of the same medium containing 0.5 mCi of L-[$^{35}$S]-methionine during which period the rate of [$^{35}$S]-methionine incorporation into cellular protein was linear. The medium was removed, the cell monolayer washed twice with phosphate-buffered saline, ph 7.4, and the soluble cytosolic proteins released by the digitonin method of Mackall, et al., supra. The remainder of the cell monolayer containing the membranous fraction was then scraped into 2.0 ml of 100 mM HEPES buffer, pH 7.5, containing 0.5% of the nonionic detergent NP-40 and 1 mM phenylmethylsulfonylfluoride. After trituration in a Pasteur pipet, the suspension was centrifuged at $10,000 \times g$ for 10 minutes at 4° C., and the supernatant saved.

[$^{35}$S]-methionine incorporation into acid insoluble material was determined by adding 20 μl of digitonin or NP-40 released material to 0.5 ml of ice cold 20% TCA with 25 μl of 0.5% bovine serum albumin added as carrier. After sitting at 4° C. for 1 hour, the mixture was centrifuged at $2,000 \times g$ for 5 minutes. The pellet was incubated in 0.5 ml of 1M NH$_4$OH at 37° for 30 minutes. The protein was reprecipitated on addition of 5.0 ml of ice cold 10% TCA and filtered on Whatman GF/C filters. The filters were extracted with diethyl ether and the amount of radiolabel determined.

F. Immunoadsorption Electrophoroesis: Aliquots of the soluble [$^{35}$S]-methionine-labeled proteins from the soluble (digitonin released) fraction of the cell monolayer were made 1 mM in PMSF and 0.5% in NP-40 detergent and then added to 5 l of either antisera specific for acetyl CoA carboxylase, or fatty acid synthetase, After 2 hours at 25° C., 100 μl of 10% IgG-SORB were added and the labeled enzymes isolated from the mixture by the method of Student, et al., supra. Polyacrylamide-SDS gels were run according to the method of Laemmli, and prepared for fluorography by use of En$^3$Hance according to the manufacturer's instructions.

G. Results—Effect of Mediator on Acetyl CoA Carboxylase and Fatty Acid Synthetase: To examine the effect of the mediator substance on the activities of acetyl CoA carboxylase and fatty acid synthetase enzymes, 3T3-L1 cells were exposed to conditioned medium from mouse peritoneal exudate cells cultured in the presence of endotoxin. After incubation of the 3T3-L1 cells with the mediator for 3, 6 and 20 hours, acetyl CoA carboxylase and fatty acid synthetase activities were determined on a digitonin released cytosolic fraction of the cells (FIG. No. 4). The activity of both enzymes decreased over the 20-hour period to approximately 25% of the initial values.

To determine if the loss in activity of the two enzymes was a result of a direct effect on protein synthesis, 3T3-L1 cells were incubated with conditioned medium from cultures of endotoxin-treated exudate cells for 3, 6, and 20 hours. During the final hour of incubation, the cells were exposed to a pulse of $^{35}$S-methionine. Following the pulse, $^{35}$S-methionine labelled acetyl CoA carboxylase and fatty acid synthetase were isolated from the digitonin releasable cytosolic fractions by immunoadsorption. Identification was accomplished by SDS-polyacrylamide gel electrophoresis and fluorography (FIGS. No. 5A and 6A). The decreased incorporation of $^{35}$S-methionine into immunoadsorbable acetyl CoA carboxylase and fatty acid synthetase with respect to time following exposure to the mediator is readily observed. Densitometric scanning of the autoradiograms (FIGS. No. 5B and 6B) indicated that after 20 hours of exposure to the mediator, the amount of $^{35}$S-methionine incorporated into fatty acid synthetase and acetyl CoA carboxylase were decreased by 80% and 95% respectively. These results are consistent with the concept that the mediator depresses the activity of acetyl CoA carboxylase and fatty acid synthetase by interfering with the synthesis of the enzyme.

H. Effect of Mediator on Protein Synthesis in General: The observed effect on acetyl CoA carboxylase and fatty acid synthetase could be explained by a general inhibition of protein synthesis by the mediator. To examine this possibility, the effect of mediator on amino acid incorporation into protein was investigated. 3T3-L1 cells were incubated for various periods of time with conditioned medium obtained from mouse peritoneal exudate cells cultured in the presence of endotoxin. $^{35}$S-methionine incorporation into soluble and membrane associated protein was determined after 1, 3, and 6 hours of exposure of the cells to the added factor. When 3T3-L1 cells were exposed to conditioned medium from mouse peritoneal exudate cells that were cultured in the absence of endotoxin, no effect on $^{35}$S-methionine in incorporation into acid insoluble protein was observed. However, as seen in FIG. No. 7, 35S-methionine incorporation into TCA precipitable material in the soluble fraction (Digitonin releasable protein) increased approximately 10% in the first 3 hours with no further change observed, while a 50% decrease was observed for label incorporation into acid insoluble material in the membrane fraction (NP-40 solubilized protein). Analysis of $^{35}$S-methionine labeled proteins following exposure to the mediator was accomplished utilizing SDS-gel electrophoresis. The pattern of the autoradiogram of the soluble proteins obtained on digitonin treatment and those solublized by NP-40 of the 3T3-L1 cells are shown in FIGS. No. 8 and 9. Closer inspection of FIG. No. 8 reveals the gradual disappearance with time following the addition of the mediator of a protein band with a molecular weight of 220,000 Daltons, while another band appears at approximately 18,000. In addition to these major changes, another new protein appears at approximately 80,000 while a second protein of 50,000 disappears.

Analysis of the NP-40 solubilized proteins showed similar results (FIG. No. 9). Protein bands of molecular weights of approximately 80,000 and 30,000 Daltons appeared while bands of approximately 220- and 50,000 disappeared.

The loss of a protein band with molecular weight 220,000 in the digitonin releasable protein, is consistent with the loss of immunoadsorbable acetyl CoA carboxylase and fatty acid synthetase. The enzymes have similar molecular weights and under the conditions of this electrophoresis migrate with the same Rm. At present, it is not possible to identify the other protein bands with known enzymes or proteins.

I. Analysis. The mediator appears to decrease enzymatic activity by suppressing the synthesis of the enzymes. The effect on protein synthesis appears to be quite specific as there are no gross perturbations of the protein patterns observed on the autoradiograms (FIGS. No. 8 and 9). In response to the mediator, the synthesis of several proteins is inhibited or induced. It was possible by immunoprecipitation to identify fatty acid synthetase and acetyl CoA carboxylase (M.W. 220,000) as two proteins whose synthesis is inhibited by the mediator. The identification of the other proteins that are modulated by the mediator is not possible at present, although lipoprotein lipase is a potential candidate for the 50,000-Dalton protein that appears. The nature of proteins that are induced in response to the mediator and the mechanism for the modulation of specific protein synthesis are deserving of further improvement investigations.

Whether the mediator responsible for regulating the synthesis of acetyl CoA carboxylase and fatty acid synthetase is the same as the mediator that suppresses the activity of lipoprotein lipase is not presently known. The relationship of these mediator(s) to the leukocyte factor that has been reported to metabolize amino acids from muscle to the liver is of considerable interest since this factor also imparts a catabolic state on the tissue.

EXAMPLE III

In this series of investigations, also embodied in an unpublished manuscript in preparation by the inventors herein, and co-worker Shigeru Sassa, we sought to determine whether the macrophage mediator(s) observed in Examples I and II exerted any effect upon red blood cell synthesis. We reasoned that, as anemia is commonly observed in mammals afflicted with chronic infections, and that as regeneration of the red cell mass constitutes a potential drain on energy and amino acids, the body in response to acute invasion may interrupt erythroid development in similar fashion and perhaps by the same mechanism observed with respect to the anabolic enzymes lipoprotein lipase, acetyl Coenzyme A carboxylase and fatty acid synthetase, that effect adipocytes.

To evaluate this hypothesis, we examined the effects of endotoxin-induced factor(s) from mouse macrophages on the cellular proliferation and differentiation of a model erythroid progenative cell—the Friend virus-transformed erythroleukemia cells (See Friend, C. et al and Marks, P. A. et al., supra.). In this model system, cells can be induced to differentiate and form hemoglobin in response to a number of inducers, such as dimethylsulfoxide, (Friend, C., et al supra.), hexamethylenebisacetamide (Reuben, R. C. et al, PROC. NATL. ACAD. SCI., U.S.A., 73: 862-866), butyric acid, (Leder, A. et al (1975) Cell 5: 319-322), and hypoxanthine (Gusella, J. F. (1976) Cell 8: 263-269). This example presents evidence that a macrophage mediator(s) can inhibit the growth and differentiation of erythroid committed cells, but has less effect on uncommitted stem cells and practically no effect on fully differentiated erythroid cells.

A. Materials: Endotoxin (lipopolysaccharide) from *E. coli* 0127: B8 isolated by the method of Westpal (described supra.), was purchased from Difco (Detroit, Mich.). A modified F12 medium was prepared in our laboratory (Sassa, S. et al, J. BIOL. CHEM. 252: 2428-2436 (1977)). Fetal bovine serum was purchased from GIBCO (Grand Island, N.Y.). Dimethylsulfoxide (Me$_2$SO) was a product of Eastman Organic Chemicals (Rochester, N.Y.). Butyric acid and hypoxanthine were obtained from Sigma Chemical Company (St. Louis, Mo.). Hexamethylenebisacetamide (HMBA) was kindly provided by Dr. R. C. Reuben, Merck Sharp & Dohme Research Laboratories (Rahway, N.J.).

B. Cell Culture: Murine Friend-virus transformed erythroleukemia cells (clone DS-19) were cultivated in modified F12 medium supplemented with 10% heat inactivated fetal bovine serum as described previously (Sassa, S., Granick, J. L., Eisen, H. and Ostertag, W. (1978) In In vitro Aspects of Erythropoiesis, ed. by Murphy, M. J. Jr. (Springer-Verlag, N.Y.) pp. 268–270).

C. Preparation of the Endotoxin-Stimulated Conditioned Medium From the Culture of Mouse Exudative Cells: Isolation of peritoneal exudate cells from NCS mice (25–33 g from the Rockefeller University Breeding Colony) and preparation in vitro of an endotoxin-stimulated conditioned medium were carried out as described (in Example I, above). Briefly, peritoneal exudate cells were isolated from mice treated with sterile Brewer's thioglycollate medium obtained from Difco Laboratories (Detroit, Mich.), in an amount of 3 ml per mouse, 6 days prior to harvest. The cells were incubated in serum-free RPM1-1640 medium for 3 hours, after which non-adherent cells were rinsed off by washing three times with medium. Cells adhering to the dish were primarily macrophages (Kawakami et al., PROC. NATL. ACAD. SCI., USA 79:912–916; Edelson, P. S. et al., J. EXP. MED., 142: 1150–1164 (1975)).

These cells were further incubated in the serum-free medium in the presence of endotoxin (5 $\mu$g/ml) for 24 hours. After incubation, the culture medium was removed and centrifuged at 1000$\times$g for 5 minutes at 4° C. The supernatant of the conditioned medium contained an endotoxin-induced mediator which decreased the activity of lipoprotein lipase in 3T3-L1 cells (as reported in Example I, above) and was used without further treatment.

D. Induction of Erythroid Differentiation: Two types of incubation protocols were used to assess erythroid differentiation of Friend cells. In certain experiments illustrated in FIGS. 10–13, the cells ($5\times 10^4$ cells/ml) were incubated at 37° C., in 5% $CO_2$ in humidified air for 18 hours. The inducing chemicals, e.g. $Me_2SO$, HMBA, butyric acid, hypoxanthine or hemin were added with or without macrophage mediator(s) and cultures were incubated for 96 hours without changing the growth medium. In other experiments such as those with results illustrated in FIG. 14, the cells ($10^5$ cells/ml) were incubated for 18 hours, then $Me_2SO$ and the macrophage mediator were added as above. The cultures were maintained at $2\times 10^5$ cells/ml by diluting the cell suspension daily with fresh medium containing the chemical inducer with or without the macrophage mediator. This procedure required more macrophage mediator than the first experimental procedure, but made it possible to examine the effect of mediator on rate of cell growth while cells were growing logarithmically at a constant rate (Chang, C. S. et al; J. BIOL. CHEM. 257: 3650–3654 (1982)).

E. Determination of Heme Content and Assays on the Activities of Enzymes In the Heme Biosynthetic Pathway: The concentration of heme in cells was determined by a fluorometric assay of prophyrin derivatives after the removal of iron (Sassa, S., Granick, S., Chang, C. and Kappas, A., In Erythropoisis, ed. by K. Nakao, J. W. Fisher and F. Takaku (University of Tokyo Press, Tokyo, Japan (1975) pp. 383–396). Cells containing hemoglobin were stained with benzidine and counted using a Cytograf model 6300A (Sassa, S., Granick, J. L., Eisen, H., and Ostertag, W., Supra.). Assays of aminolevulinic acid (ALA) dehydratase and porphobilinogen (PBG) deaminase were carried out by methods described previously (Sassa, S., Granick, J. H., Eisen, H., and Ostertag, W., Supra.).

Figure 10:
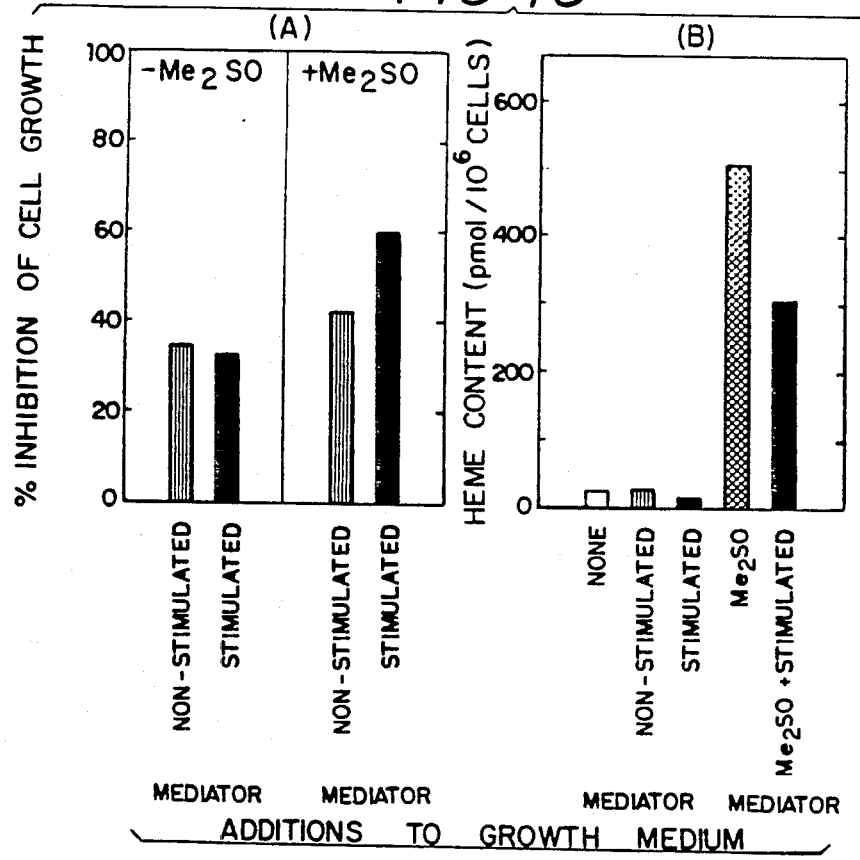
FIG. 10 shows the effect of conditioned media from mouse macrophage cultures on the cell growth and heme content in Friend cells.

F. Effects of the Macrophage Mediator on the Growth and Differentiation of Uninduced Friend Cells: Conditioned media from macrophage cultures incubated with or without endotoxin inhibited the growth of untreated Friends cells by approximately 35% (FIG. 10, Part A.). When these cells were incubated simultaneously with 1.5% $Me_2SO$, control conditioned medium which had not been exposed to endotoxin inhibited the cell growth by ~42% while endotoxin-stimulated conditioned medium inhibited the growth of ~60% (FIG. 10, Part B).

Heme content in these cells treated with endotoxin-stimulated or non-stimulated conditioned media was not appreciably different from that found in untreated cells, indicating that the conditioned medium by itself does not affect the erythroid differentiation of Friend cells (FIG. 10, Part B). In contrast, incubation of cells with $Me_2SO$ and endotoxin-stimulated conditioned medium led to a significant decrease (~40%) in the heme content in the cell (FIG. 10, Part B).

G. Dose Dependent Inhibition of Cell Growth and Differentiation By the Macrophage Mediator: When Friend cells were incubated simultaneously with 1.5% $Me_2SO$ and the endotoxin-stimulated macrophage mediator, the rate of cell growth was progressively inhibited when increasing amounts of the mediator were added to the culture (FIG. 11, Part A). An inhibitory effect of the mediator on cell growth could be detected at the lowest concentration examined (1.12 vol. % added to growth medium). At the highest concentration (8 vol. %), the mediator inhibited cell growth by ~60% compared with that of the control $Me_2SO$-treated culture (FIG. 11, Part A). The decrease in cell number was not due to cell death since the number of dead cells as accessed by the Trypan Blue exclusion test (Paul J. In Cell Culture) was similar (~8%) for untreated controls and cultures treated with the stimulated conditioned medium. Endotoxin itself (up to 15 $\mu$g/ml) exhibited no inhibitory effect on the growth of Friend cells either in the presence or in the absence of $Me_2SO$ (data not shown). These findings indicate that the endotoxin-stimulated macrophage mediator interferes with the growth of $Me_2SO$-treated cells more than that of untreated cells and suggest that erythroid committed cells may be more sensitive than uncommitted stem cells to the action of the stimulated macrophage mediator.

Treatment of cells with the endotoxin-stimulated macrophage mediator inhibited $Me_2So$-mediated erythroid differentiation resulting in a progressive decrease in the content of porphyrin and heme in the treated cells as the amount of the mediator increased (FIG. 11, Part B). The enzymatic activities of ALA dehydratase and PBG deaminase were also decreased by the mediator treatment (FIG. 11, Part B). The addition of the macrophage mediator directly to the enzyme assay mixture did not inhibit the activity of ALA dehydratase or PBG Deaminase (data not shown), ruling out a direct inhibitory effect on the activities of the enzymes.

H. Delayed Addition of the Endotoxin-Stimulated Macrophage Mediator on Erythroid Differentiator: When the endotoxin-stimulated conditioned medium was added to $Me_2SO$-treated cultures at various times, it was found that the effect of the macrophage mediator on cell growth was gradually lost (FIG. 12).

The effect of the macrophage mediator on erythroid differentiation decreased more rapidly than the effect on cell growth. For example, the addition of the endotoxin-stimulated macrophage mediator inhibited heme and protoporphyrin formation by ~40% at the beginning of incubation, ~25% when added at 24 hours, and had no effect when added at 48 hours or after. Inhibition of the activity of ALA dehydratase and PBG deaminase by the macrophage mediator treatment was also progressively diminished when the mediator was added later during incubation (FIG. 12).

These findings indicate that, in contrast to the macrophage-mediator dependent inhibition of cell growth and differentiation observed in erythroid-committed cells, cells which have fully expressed erythroid characteristics such as those exhibiting maximal increases in the activities of ALA dehydratase and PBG deaminase, or in the contents of protoporphyrin and heme, are considerably less sensitive to the inhibitory effect of the macrophage mediator.

I. Effects of The Endotoxin-Stimulated Macrophage Mediator On Erythroid Differentiation of Friend Cells Induced by HMBA, Butyric Acid, Hypoxanthine or Hemin: In order to examine whether or not the inhibitory effect of the endotoxin-stimulated macrophage mediator on erythroid committed cells is specific for Me$_2$SO-induced differentiation, we examined the effect of the macrophage mediator on cells which were incubated with either HMBA, butyric acid, hypoxanthine, or hemin. We found that the endotoxin-stimulated macrophage mediator markedly inhibited the growth of cells incubated with HMBA, butyric acid or hypoxanthine, but not the growth of hemin-treated cells (FIG. 13, Part A). Similarly, the endotoxin-stimulated mediator inhibited the erythroid differentiation induced by HMBA, butyric acid or hypoxanthine, but not that induced by hemin treatment (FIG. 13, Part B).

These findings suggest that the inhibitory action of the endotoxin-stimulated macrophage mediator on the growth of erythroid-committed cells and erythroid differentiation induced by most of the chemical agents as represented by Me$_2$SO, HMBA, butyric acid or hypoxanthine is similar, but that erythroid differentiation induced by hemin treatment is distinct in nature and not sensitive to the effect of the macrophage mediator. In fact the growth inhibition of Me$_2$SO-treated cells produced by the macrophage mediator alone (35%, FIG. 10) was completely overcome by hemin treatment (FIG. 13).

J. Effect of Endotoxin-Stimulated Macrophage Mediator on the Growth and Differentiation of Friend Cells Growing at a Constant Rate: In order to examine the effect of the macrophage mediator on the growth of Friend cells while they are growing at a constant rate, cells were diluted with fresh medium with or without the mediator every 24 hours to reduce the cell density to $2 \times 10^5$ cells/ml.

Under these conditions of culture, the cells maintain a continuous logarithmic growth at a constant rate (Chang,). C. S. et al supra.) The total number of cells that would have formed from the original untreated control culture was $82 \times 10^6$ cells/ml after 96 hours of incubation (FIG. 14). The addition of the macrophage mediator significantly inhibited (~70%) cell growth. The addition of Me$_2$SO to the cultures yielded $42 \times 10^6$ cells/ml. This decrease probably reflects the growth cessation which is associated with terminal erythroid differentiation of these cells. (Chang, C. S. supra.; Lo, S.C., Aft., R. and Mueller, G. C., Cancer Res. 41: 864–870 (1981)). Combined addition of Me$_2$SO and the macrophage mediator produced the most profound growth inhibition (~90%) of these cells. Heme content in cells treated with the mediator alone was not appreciably affected while the combined treatment with the mediator and Me$_2$SO brought about ~40% inhibition of heme formation.

K. Analysis: The mediator substance under study appears to potently inhibit the growth and erythroid differentiation of mouse Friend-virus transformed cells. Conditioned medium from cultures not exposed to endotoxin had some inhibitory effects, but the effect of the endotoxin-stimulated conditioned medium is significantly greater in inhibiting the growth and differentiation of Friend cells. Endotoxin itself had no effect on either cell growth or differentiation.

Further, the effect of the mediator appears to be specific to certain stages of erythroid progenitor cells, in that the macrophage mediator inhibited the growth and erythroid differentiation of uncommitted stem cells more than that of erythroid committed cells which were induced by treatment with Me$_2$SO, HMBA, butyric acid or hypoxanthine. The inhibitory effect of the macrophage mediator on cell growth was more pronounced in cells growing logarithmically at a constant rate. Hemin treatment of Friend cells is known to cause erythroid cells maturation leading to the appearance of hemoglobinized cells but without accompanying the commitment of undifferentiated stem cells to the erythroid precursor cells (Gusella, J. F., Weil, S. C., Tsiftsoglon, A. S., Volloch, V., Neuman, J. R. and Housman, D. (1976) Blood 56: 481–487). Interestingly, the endotoxin-stimulated macrophage mediator also had very little effect on the growth and differentiation of Friend cells in the presence of hemin.

These results indicate that the endotoxin-stimulated macrophage mediator exerts its inhibitory effect on the growth and differentiation of cells of erythroid precursor cells including those which have been committed to undergo erythroid differentiation. On the other hand, cells which have fully expressed characteristics of erythroid cells such as increased activities of ALA dehydratase and PBG deaminase, and increased contents of protoporphyrin and heme are no longer sensitive to the inhibitory effect of the conditioned medium. Thus it appears that the action of the endotoxin-stimulated conditioned medium is relatively specific to certain early stages of erythroid precursor cells but not to fully differentiated erythroid cells.

We have also attempted to purify the mediator from the endotoxin-stimulated macrophage conditioned medium and found that a highly purified mediator retained the inhibitory property both on lipoprotein lipase activity in 3T3 cells and on the growth and differentiation of Friend cells.

The macrophage factor described in this Example is believed to play a role in the pathogenesis of the anemia associated with endotoxemia or other chronic disease states, e.g., cancer, rheumatoid arthritis, where the activity of the reticuloendothelial system is stimulated. The Friend cell system described here should be useful to detect such in vivo mediators and to elucidate the biochemical basis for the cellular effect of the mediator(s). This assay system should also aid the isolation of this factor and the identification of its relationship with other immune cell factors which are produced in response to invasion.

We claim:

1. A pharmaceutical composition for the treatment of obesity in humans, comprising:
   A. a proteinaceous mediator substance capable of suppressing the activity of the anabolic enzymes lipoprotein lipase, acetyl Coenzyme A carboxylase and fatty acid synthetase, and inhibiting the growth and differentiation of erythroid-committed cells, or a specific binding partner thereto, wherein said mediator substance exhibits molecular weight levels of about 300,000, 70,000 and in the range of 400 to 1000 Daltons as determined by gel electrophoresis, and is derived from animal macrophage cells that have been incubated with a stimulator material that accompanies an invasive stimulus; and
   B. a pharmaceutically effective carrier.

2. The composition of claim 1 wherein said mediator substance is further capable of inhibiting the differentiation of fat cells, and increasing the activity of hormone-sensitive lipase in fat cells and the uptake of glucose in muscle cells, while demonstrably lacking leucocyte activator activity and the ability to cause either fever or muscle protein degradation.

* * * * *